US009452165B2

(12) United States Patent
El-Deiry et al.

(10) Patent No.: US 9,452,165 B2
(45) Date of Patent: *Sep. 27, 2016

(54) SMALL MOLECULE TRAIL GENE INDUCTION BY NORMAL AND TUMOR CELLS AS AN ANTICANCER THERAPY

(71) Applicant: The Penn State Research Foundation, University Park, PA (US)

(72) Inventors: Wafik S. El-Deiry, Bryn Mawr, PA (US); Joshua E. Allen, Hershey, PA (US); Gen Sheng Wu, Troy, MI (US)

(73) Assignee: THE PENN STATE RESEARCH FOUNDATION, University Park, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/733,740

(22) Filed: Jun. 8, 2015

(65) Prior Publication Data

US 2015/0265619 A1 Sep. 24, 2015

Related U.S. Application Data

(60) Continuation of application No. 14/192,329, filed on Feb. 27, 2014, now Pat. No. 9,061,032, which is a division of application No. 13/459,775, filed on Apr. 30, 2012, now Pat. No. 8,673,923.

(60) Provisional application No. 61/480,743, filed on Apr. 29, 2011.

(51) Int. Cl.
| | | |
|---|---|---|
| *A61K 31/519* | (2006.01) | |
| *A61K 31/4188* | (2006.01) | |
| *A61K 31/4545* | (2006.01) | |
| *A61K 31/513* | (2006.01) | |
| *A61K 31/337* | (2006.01) | |
| *A61K 39/395* | (2006.01) | |
| *A61K 45/06* | (2006.01) | |
| *G01N 33/68* | (2006.01) | |
| *A61K 39/00* | (2006.01) | |

(52) U.S. Cl.
CPC ............ *A61K 31/519* (2013.01); *A61K 31/337* (2013.01); *A61K 31/4188* (2013.01); *A61K 31/4545* (2013.01); *A61K 31/513* (2013.01); *A61K 39/3955* (2013.01); *A61K 39/39558* (2013.01); *A61K 45/06* (2013.01); *G01N 33/6863* (2013.01); *A61K 2039/505* (2013.01); *G01N 2800/52* (2013.01)

(58) Field of Classification Search
CPC .................. A61K 31/337; A61K 31/39558; A61K 31/4188; A61K 31/4545; A61K 31/513; A61K 31/519
See application file for complete search history.

(56) References Cited

U.S. PATENT DOCUMENTS

| | | | |
|---|---|---|---|
| 5,648,097 | A | 7/1997 | Nuwayser |
| 6,136,345 | A | 10/2000 | Grimmett et al. |
| 6,630,486 | B1 | 10/2003 | Royer |
| 2008/0004286 | A1 | 1/2008 | Wang et al. |
| 2014/0271540 | A1 | 9/2014 | Stogniew et al. |

FOREIGN PATENT DOCUMENTS

| | | |
|---|---|---|
| DE | 2150062 | 4/1973 |
| WO | WO 03/037913 A2 | 5/2003 |
| WO | WO03/055489 | 7/2003 |
| WO | WO 2007/090794 A1 | 8/2007 |
| WO | WO 2010/009985 A2 | 1/2010 |
| WO | WO 2010/149357 A2 | 12/2010 |

OTHER PUBLICATIONS

Bevis et al. "Anti-tumor activity of an anti-DR5 monoclonal antibody, TRA-8, in combination with taxane/platinum-based chemotherapy in an ovarian cancer model", Gynecol Oncol. Apr. 2011;121(1):193-9.
Chen et al. "Cisplatin-enhanced sensitivity of glioblastoma multiforme U251 cells to adenovirus-delivered TRAIL in vitro", Tumour Biol. Dec. 2010;31(6):613-22.
Hetschko et al. "Upregulation of DR5 by proteasome inhibitors potently sensitizes glioma cells to TRAIL-induced apoptosis", FEBS J. Apr. 2008;275(8):1925-36.
Nagane et al. "Increased death receptor 5 expression by chemotherapeutic agents in human gliomas causes synergistic cytotoxicity with tumor necrosis factor-related apoptosis-inducing ligand in vitro and in vivo", Cancer Res. Feb. 15, 2000;60(4):847-53.
Siegelin et al. "KAAD-cyclopamine augmented TRAIL-mediated apoptosis in malignant glioma cells by modulating the intrinsic and extrinsic apoptotic pathway", Neurobiol Dis. May 2009;34(2):259-66.
Sung et al. "Celastrol, a triterpene, enhances TRAIL-induced apoptosis through the down-regulation of cell survival proteins and up-regulation of death receptors", J Biol Chem. Apr. 9, 2010;285(15):11498-507.
Yoshida et al. "Kaempferol sensitizes colon cancer cells to TRAIL-induced apoptosis", Biochem Biophys Res Commun. Oct. 10, 2008;375(1):129-33.
Yoshida et al. "Lipoxygenase inhibitors induce death receptor 5/TRAIL-R2 expression and sensitize malignant tumor cells to TRAIL-induced apoptosis", Cancer Sci. Sep. 2007;98(9):1417-23.
Abdulghani, J. et al., TRAIL receptor signaling and therapeutics, *Expert Opinion on Therapeutic Targets*, 2010 ,(10)14.
Allen, J. et al., Potent anti-tumor effects of TIC10 require F0x03a and TRAIL gene upregulation, *Cancer Research*, (8)72Supp , Apr. 1, 2012 ,15(Abstract).

(Continued)

*Primary Examiner* — Yong Chong
(74) *Attorney, Agent, or Firm* — Pearl Cohen Zedek Latzer Baratz LLP

(57) ABSTRACT

Methods and compositions relating to TIC10 are described according to aspects of the present invention. The compositions and methods have utility in treating disease, particularly cancer in a subject in need thereof, including a human subject as well as subjects of other species. The compositions have utility in treating brain cancer in a subject in need thereof.

22 Claims, 27 Drawing Sheets

(56) References Cited

OTHER PUBLICATIONS

Allen, J. et al., Targeting TRAIL death receptor 4 with trivalent DR4 Atrimer complexes, *Molecular Cancer Therapeutics*, pp., Jul. 1-28, 2012, 16.

Allen et al. "The small molecule TIC10 has potent anticancer efficacy mediated by induction of TRAIL production in normal and tumor cells", Cancer Res Apr. 15, 2011 71; 4502.

Ashkenazi, A. et al., Safety and antitumor activity of recombinant soluble Apo2 ligand, *Journal of Clinical Investigations*, 102:155-162,1999.

Camidge, D. et al., A Phase I Safety and Pharmacokinetic Study of the Death Receptor 5 Agonistic Antibody PRO95780 in Patients with Advanced Malignancies, *Clinical Cancer Research*, 2010, 1256-1263:16.

Dorsey J., et al, Tumor necrosis factor-related apoptosis-inducing ligand (TRAIL) and paclitaxel have cooperative in vivo effects against glioblastoma multiforme cells, *Mol. Cancer Ther.*, 3285-3295:8, 2009.

Greco, F. et al., Phase 2 study of mapatumumab, a fully human agonistic monoclonal antibody which targets and activates the TRAIL receptor-1, in patients with advanced non-small cell lung cancer, Lung Cancer, 2008, 82-90:61.

Griffith, T. et al., Adenoviral-mediated transfer of the TNF-related apoptosis-inducing ligand/Apo-2 ligand gene induces tumor cell apoptosis, J Immunol, 2000, 2886-94:165.

Leong, S. et al., Mapatumumab, an Antibody Targeting TRAIL-R1, in Combination With Paclitaxel and Carboplatin in Patients With Advanced Solid Malignancies: Results of a Phase I and Pharmacokinetic Study, J Clin Oncol, 2009, 4413-4421:27.

Mom, C. et al., Mapatumumab, a Fully Human Agonistic Monoclonal Antibody That Targets TRAIL-R1, in Combination with Gemcitabine and Cisplatin: a Phase I Study, Clinical Cancer Research, 2009, 5584-5590:15.

NCI-60 DTP Human Tumor Cell Line Screen, downloaded Feb. 26, 2011.

Plummer, R. et al., Phase 1 and Pharmacokinetic Study of Lexatumumab in Patients with Advanced Cancers, Clinical Cancer Research, 2007, 6187-6194:13.

PubChem Database entry for compound NSC350625, downloaded Jan. 19, 2011.

Singh T., et al, Synergistic interactions of chemotherapeutic drugs and tumor necrosis factor related apoptosis-inducing ligand/Apo-2 ligand on apoptosis and on regression of breast carcinoma in vivo, Cancer Res., 2003 63(17):5390-400.

Tolcher, A. et al., Phase I Pharmacokinetic and Biologic Correlative Study of Mapatumumab, a Fully Human Monoclonal Antibody With Agonist Activity to Tumor Necrosis Factor Related Apoptosis-inducing Ligand Receptor-1, J Clin Oncol, 2007, 25:1390-1396.

Trarbach, T. et al., Phase II trial of mapatumumab, a fully human agonistic monoclonal antibody that targets and activates the tumour necrosis factor apoptosis-inducing ligand receptor-1 (TRAIL-R1, (in patients with refractory colorectal cancer, *British Journal of Cancer*, 2010, 102:506-512.

Patel, L., Apoptotic Induction via Small Molecule Compounds, A thesis in Chemistry, Jun. 16, 2010.

International Search Report for PCT/US12/35831, dated Oct. 29, 2012.

Written Opinion for PCT/US12/35831, dated Oct. 29, 2012.

Supplementary European Search Report for European Patent Application No. 12776073.4 dated Dec. 4, 2014.

Jacob et al., "Pharmacophore Reassignment for Induction of the Immunosurveillance Cytokine TRAIL", Angew. Chem. Int. Ed. 2014, 53, 1-5.

Allen et al., Dual Inactivation of Akt and ERK by TIC10 Signals Foxo3a Nuclear Translocation, TRAIL Gene Induction, and Potent Antitumor Effects www.sciencetranslationmedicine.org vol. 5 Issue 171, 2013.

Wagner et al., "The angular structure of ONC201, a TRAIL pathway-inducing compound, determines its potent anti-cancer activity", Oncotarget vol. 5, No. 24, Jan. 2015.

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: forward primer for TRAIL

<400> SEQUENCE: 1
cagaggaaga agcaacacat t                                                 21

<210> SEQ ID NO 2
<211> LENGTH: 28
<212> TYPE: DNA
<213> ORGANISM: Artificial Sequence
<220> FEATURE:
<223> OTHER INFORMATION: reverse primer for TRAIL

<400> SEQUENCE: 2
ggttgatgat tcccaggagt ttattttg                                          28

<210> SEQ ID NO 3
<211> LENGTH: 20
<212> TYPE: DNA
<213> ORGANISM: Artificial Sequence
<220> FEATURE:
<223> OTHER INFORMATION: forward primer for GAPDH

<400> SEQUENCE: 3
ccacatcgct cagacaccat                                                   20

<210> SEQ ID NO 4
<211> LENGTH: 26
<212> TYPE: DNA
<213> ORGANISM: Artificial Sequence
```

```
<220> FEATURE:
<223> OTHER INFORMATION: reverse primer for GAPDH

<400> SEQUENCE: 4
ggcaacaata tccactttac cagagt                                    26
```

SMALL MOLECULE TRAIL GENE INDUCTION BY NORMAL AND TUMOR CELLS AS AN ANTICANCER THERAPY

REFERENCE TO RELATED APPLICATION

This application is a continuation of U.S. patent application Ser. No. 14/192,329, filed 27 Feb. 2014, now allowed, which is a divisional of U.S. patent application Ser. No. 13/459,775, filed 30 Apr. 2012, now issued as U.S. Pat. No. 8,673,923, which in turn claims priority to, and the benefit of, U.S. Provisional Patent Application No. 61/480,743, filed 29 Apr. 2011, the entire contents of which are incorporated herein by reference.

GRANT REFERENCE

This invention was made with government support under Grant No. U54 CA105008, awarded by the National Institutes of Health. The Government has certain rights in the invention.

FIELD OF THE INVENTION

The present invention relates generally to methods and compositions for treating proliferative disease, such as cancer, in a subject in need thereof.

BACKGROUND OF THE INVENTION

TNF-related apoptosis-inducing ligand (TRAIL; Apo2L) is an endogenous protein that selectively induces apoptosis in cancer cells.

TRAIL is a powerful inducer of apoptosis in a wide range of human cancer cell lines via pro-apoptotic death receptor 4 (DR4; TRAIL-R1) and death receptor 5 (DR5; TRAIL-R2) at the cell surface through engagement of the extrinsic or intrinsic apoptotic pathways. TRAIL plays a direct role in tumor suppression during immune surveillance but this anti-tumor mechanism is lost during the disease progression. The ability of TRAIL to initiate apoptosis selectively in cancer cells has led to ongoing clinical trials with administration of recombinant TRAIL and the longer-lived TRAIL-agonist antibodies targeting either of its two pro-apoptotic death receptors.

Despite its potency, recombinant TRAIL has efficacy-limiting properties such as short serum half-life, stability, cost, and delivery. Delivery of recombinant TRAIL or TRAIL-agonist antibodies to the brain is limited by inability of recombinant TRAIL and TRAIL-agonist antibodies to cross the blood-brain bather.

There is a continuing need for anti-cancer compositions and methods.

SUMMARY OF THE INVENTION

Pharmaceutical compositions including

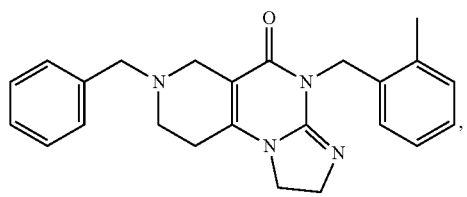

(I)

also called TIC10 herein, a pharmaceutically acceptable derivative, salt, ester, amide, hydrate, solvate and/or prodrug thereof; and a pharmaceutically acceptable carrier, are provided according to aspects of the present invention. The compositions have utility in treating disease in a subject in need thereof, including a human subject as well as subjects of other species. The compositions have utility in treating cancer in a subject in need thereof, including a human subject as well as subjects of other species.

According to aspects of the present invention, pharmaceutical compositions are provided which include TIC10, a pharmaceutically acceptable derivative, salt, ester, amide, hydrate, solvate and/or prodrug thereof; a pharmaceutically acceptable carrier; and a second therapeutic agent.

According to aspects of the present invention, pharmaceutical compositions are provided which include TIC10, a pharmaceutically acceptable derivative, salt, ester, amide, hydrate, solvate and/or prodrug thereof; a pharmaceutically acceptable carrier; and a second anti-cancer agent, wherein TIC10, a pharmaceutically acceptable derivative, salt, ester, amide, hydrate, solvate and/or prodrug thereof is the first anti-cancer agent.

According to aspects of the present invention, pharmaceutical compositions are provided which include TIC10, a pharmaceutically acceptable derivative, salt, ester, amide, hydrate, solvate and/or prodrug thereof; a pharmaceutically acceptable carrier; and a mitotic inhibitor.

According to aspects of the present invention, pharmaceutical compositions are provided which include TIC10, a pharmaceutically acceptable derivative, salt, ester, amide, hydrate, solvate and/or prodrug thereof; a pharmaceutically acceptable carrier; and paclitaxel, docetaxel or a combination thereof.

According to aspects of the present invention, pharmaceutical compositions are provided which include TIC10, a pharmaceutically acceptable derivative, salt, ester, amide, hydrate, solvate and/or prodrug thereof; a pharmaceutically acceptable carrier; and an anti-angiogenic agent.

According to aspects of the present invention, pharmaceutical compositions are provided which include TIC10, a pharmaceutically acceptable derivative, salt, ester, amide, hydrate, solvate and/or prodrug thereof; a pharmaceutically acceptable carrier; and bevacizumab.

According to aspects of the present invention, pharmaceutical compositions formulated for oral administration are provided which include TIC10, a pharmaceutically acceptable derivative, salt, ester, amide, hydrate, solvate and/or prodrug thereof; and a pharmaceutically acceptable carrier.

Methods of treatment of a subject in need thereof are provided according to aspects of the present invention which include administering a pharmaceutically effective amount of TIC10, a pharmaceutically acceptable derivative, salt, ester, amide, hydrate, solvate and/or prodrug thereof; and a pharmaceutically acceptable carrier.

Methods of treatment of a subject having, or at risk of having, cancer are provided according to aspects of the present invention which include administering a pharmaceutically effective amount of TIC10, a pharmaceutically acceptable derivative, salt, ester, amide, hydrate, solvate and/or prodrug thereof; and a pharmaceutically acceptable carrier.

Methods of treatment of a subject having, or at risk of having, cancer are provided according to aspects of the present invention which include administering a pharmaceutically effective amount of TIC10; and a pharmaceutically acceptable carrier.

Methods of treatment of a subject having, or at risk of having, cancer are provided according to aspects of the present invention which include administering a pharmaceutically effective amount of a pharmaceutically acceptable derivative of TIC10; and a pharmaceutically acceptable carrier.

Methods of treatment of a subject having, or at risk of having, cancer are provided according to aspects of the present invention which include administering a pharmaceutically effective amount of TIC10, a pharmaceutically acceptable salt, ester, amide, hydrate and/or solvate thereof; and a pharmaceutically acceptable carrier.

Methods of treatment of a subject having, or at risk of having, cancer are provided according to aspects of the present invention which include administering a pharmaceutically effective amount of TIC10 or a pharmaceutically acceptable salt, hydrate or solvate thereof; and a pharmaceutically acceptable carrier.

Methods of treatment of a subject having, or at risk of having, cancer are provided according to aspects of the present invention which include administering a pharmaceutically effective amount of TIC10, a pharmaceutically acceptable derivative, salt, ester, amide, hydrate, solvate and/or prodrug thereof; and a pharmaceutically acceptable carrier; and further including assaying TNF-related apoptosis-inducing ligand in a sample obtained from the subject to assess the effect of the treatment.

Methods of treatment of a subject having, or at risk of having, cancer are provided according to aspects of the present invention which include administering a pharmaceutically effective amount of TIC10, a pharmaceutically acceptable derivative, salt, ester, amide, hydrate, solvate and/or prodrug thereof; and a pharmaceutically acceptable carrier; and further including assaying TNF-related apoptosis-inducing ligand in a blood, serum, plasma or cerebrospinal fluid sample obtained from the subject to assess the effect of the treatment.

Methods of treatment of a subject having, or at risk of having, cancer are provided according to aspects of the present invention which include administering a pharmaceutically effective amount of TIC10, a pharmaceutically acceptable derivative, salt, ester, amide, hydrate, solvate and/or prodrug thereof; and a pharmaceutically acceptable carrier; and further including administering a therapeutically effective amount of a second anti-cancer agent, wherein TIC10, the pharmaceutically acceptable derivative, salt, ester, amide, hydrate, solvate and/or prodrug thereof is the first anti-cancer agent.

Methods of treatment of a subject having, or at risk of having, cancer are provided according to aspects of the present invention which include administering a pharmaceutically effective amount of TIC10, a pharmaceutically acceptable derivative, salt, ester, amide, hydrate, solvate and/or prodrug thereof; and a pharmaceutically acceptable carrier; and further including administering a therapeutically effective amount of an anti-mitotic agent.

Methods of treatment of a subject having, or at risk of having, cancer are provided according to aspects of the present invention which include administering a pharmaceutically effective amount of TIC10, a pharmaceutically acceptable derivative, salt, ester, amide, hydrate, solvate and/or prodrug thereof; and a pharmaceutically acceptable carrier; and further including administering a therapeutically effective amount of paclitaxel, docetaxel, bevacizumab or any two or more thereof.

Methods of treatment of a subject having, or at risk of having, cancer are provided according to aspects of the present invention which include oral administration a pharmaceutically effective amount of TIC10, a pharmaceutically acceptable derivative, salt, ester, amide, hydrate, solvate and/or prodrug thereof; and a pharmaceutically acceptable carrier.

Methods of treatment of a subject having, or at risk of having, cancer are provided according to aspects of the present invention which include administering a pharmaceutically effective amount of TIC10, a pharmaceutically acceptable derivative, salt, ester, amide, hydrate, solvate and/or prodrug thereof; and a pharmaceutically acceptable carrier, wherein the administering is by a route selected from the group consisting of: rectal, nasal, pulmonary, epidural, ocular, otic, intraarterial, intracardiac, intracerebroventricular, intradermal, intravenous, intramuscular, intraperitoneal, intraosseous, intrathecal, intravesical, subcutaneous, topical, transdermal, transmucosal, sublingual, buccal, vaginal, and inhalational routes of administration.

Methods of treatment of a subject having, or at risk of having, brain cancer are provided according to aspects of the present invention which include administering a pharmaceutically effective amount of TIC10, a pharmaceutically acceptable derivative, salt, ester, amide, hydrate, solvate and/or prodrug thereof; and a pharmaceutically acceptable carrier.

BRIEF DESCRIPTION OF THE DRAWINGS

FIG. 67 is a graph showing surface TRAIL induction as in FIG. 66 with or without stable knockdown of Foxo3a;

DETAILED DESCRIPTION OF THE INVENTION

Figure 1:
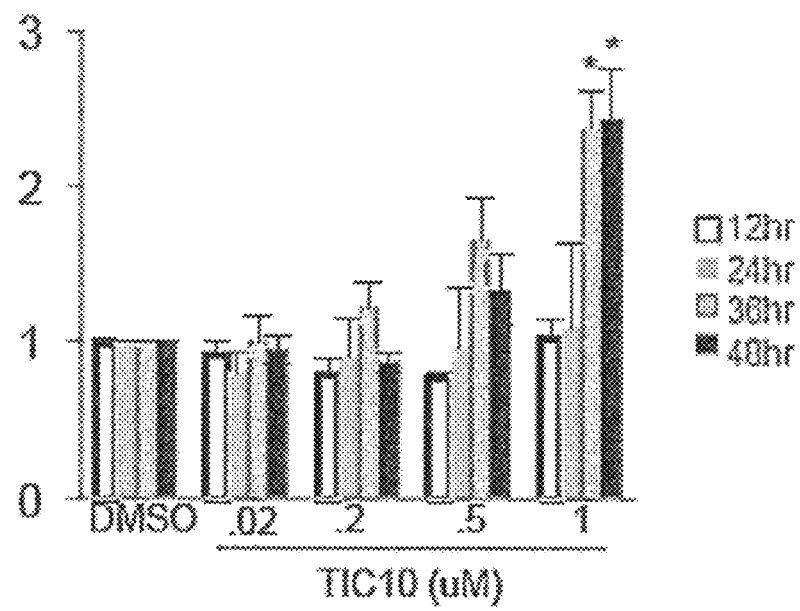
FIG. 1 is a graph showing activity of luciferase reporter in HCT116 Bax$^{-/-}$ cells under transcriptional control of the first 504 base pairs of the human TRAIL gene promoter upstream of the start of transcription.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W. H. Freeman & Company, 2004; Engelke, D. R., RNA Interference (RNAi): Nuts and Bolts of RNAi Technology, DNA Press LLC, Eagleville, Pa., 2003; Herdewijn, P. (Ed.), Oligonucleotide Synthesis: Methods and Applications, Methods in Molecular Biology, Humana Press, 2004; A. Nagy, M. Gertsenstein, K. Vintersten, R. Behringer, Manipulating the Mouse Embryo: A Laboratory Manual, 3rd edition, Cold Spring Harbor Laboratory Press; Dec. 15, 2002, ISBN-10: 0879695919; Kursad Turksen (Ed.), Embryonic stem cells: methods and protocols in Methods Mol Biol. 2002; 185, Humana Press; Current Protocols in Stem Cell Biology, ISBN: 9780470151808.

The singular terms "a," "an," and "the" are not intended to be limiting and include plural referents unless explicitly state or the context clearly indicates otherwise.

Methods and compositions according to aspects of the present invention relate to TRAIL-inducing compound 10 (TIC10), identified by the present inventors as a small molecule transcriptional inducer of the TRAIL gene by a screen for TRAIL-inducing compounds that upregulate the TRAIL gene by a mechanism that does not rely on p53 since p53 is frequently inactivated in late stage cancers, which causes resistance to many standard-of-care therapies such as 5-FU and doxorubicin.

TIC10 induces TRAIL expression in both normal and cancer cells. The terms "induces TRAIL expression," "TIC10-induced TRAIL" and grammatical equivalents thereof, used herein to describe an effect of TIC10 or a pharmaceutically acceptable derivative, salt, ester, amide, hydrate, solvate and/or prodrug thereof, refers to production of a detectable increase of TRAIL by cells contacted with TIC10 or a pharmaceutically acceptable derivative, salt, ester, amide, hydrate, solvate and/or prodrug thereof. A detectable increase of TRAIL can be determined by assays for TRAIL protein or TRAIL nucleic acids using well-known protein or nucleic acid assay methodology.

TIC10-induced TRAIL is sustained in cancer cells as well as normal cells and serum, allowing for a TRAIL-mediated bystander effect on cancer cells and tumors. TIC10 inactivates Akt and ERK leading to the nuclear translocation of Foxo3a and induction of TRAIL transcription.

TIC10-induced TRAIL is dependent on Foxo3a, which also upregulates TRAIL death receptor DR5 among other targets, allowing for sensitization of some TRAIL-resistant tumor cells. The induction of TRAIL caused by TIC10 is sustained in tumor, stromal, and host cells.

Pharmaceutical compositions including TIC10 or a pharmaceutically acceptable derivative, salt, ester, amide, hydrate, solvate and/or prodrug thereof, and methods for their use are provided according to aspects of the present invention.

Pharmaceutical compositions including the compound of structure (I) are provided according to aspects of the present invention.

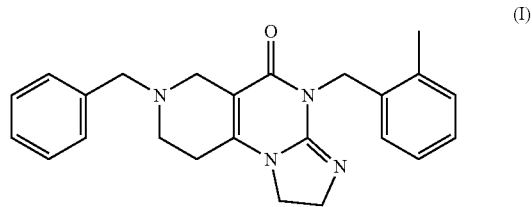 [SMILES: Cc1ccccc1CN1C(=O)C2=C(CCN(Cc3ccccc3)C2)N2CCN=C12]

(I)

The compound of structure (I) is also referred to herein as TRAIL-inducing compound 10 (TIC10) and NSC350625.

The compound of structure (I) (TIC10) can be obtained commercially or synthesized using standard chemical synthetic methodology.

A pharmaceutical composition according to aspects of the present invention may also be a pharmaceutically acceptable derivative, salt, ester, amide, hydrate, solvate and/or prodrug of the compound of structure (I).

Pharmaceutically acceptable derivatives, salts, esters, amides, hydrates, solvates and/or prodrugs of the compound of structure (I) can be obtained commercially or synthesized using standard chemical synthetic methodology.

The term "pharmaceutically acceptable derivative" as used in relation to of the compound of structure (I) is the compound of structure (I) further substituted at any substitutable position which substantially retains the described activity of the compound of structure (I) to induce expression of TRAIL in a cell. For example, the compound of structure (I) is optionally further substituted at any substitutable position by one or more of the following: F, Cl, Br, a lower alkyl group, a lower alkoxy group or fluorinated lower alkyl group, such as CF₃.

A "pharmaceutically acceptable" salt, ester, amide hydrate, prodrug, or solvate is suitable for use in a subject without undue toxicity or irritation to the subject and is effective for the intended use.

Pharmaceutically acceptable salts include pharmaceutically acceptable acid addition salts and base addition salts. Pharmaceutically acceptable salts are well-known in the art, such as those detailed in S. M. Berge et al., J. Pharm. Sci., 66:1-19, 1977. Exemplary pharmaceutically acceptable salts are those suitable for use in a subject without undue toxicity or irritation to the subject and which are effective for their intended use which are formed with inorganic acids such as hydrochloric acid, hydrobromic acid, hydroiodic acid, nitric acid, phosphoric acid, sulfuric acid and sulfamic acid; organic acids such as acetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, formic acid, fumaric acid, glutamic acid, glycolic acid, glycerophosphoric acid, hemisulfic acid, heptanoic acid, hexanoic acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, trichloroacetic acid, trifluoroacetic acid and undecanoic acid; inorganic bases such as ammonia, hydroxide, carbonate, and bicarbonate of ammonium; organic bases such as primary, secondary, tertiary and quaternary amine compounds ammonium, arginine, betaine, choline, caffeine, diolamine, diethylamine, diethanolamine, 2-dimethylaminoethanol, 2-diethylaminoethanol, dicyclohexylamine, dicyclohexylamine, dibenzylamine, N,N-dibenzylphenethylamine, 1-ephenamine, N,N'-dibenzylethylenediamine, ethanolamine, ethylamine, ethylenediamine, glucosamine, histidine, hydrabamine, isopropyl amine, 1h-imidazole, lysine, methylamine, N-ethylpiperidine, N-methylpiperidine, N-methylmorpholine, N,N-dimethylaniline, piperazine, trolamine, methylglucamine, purines, piperidine, pyridine, theobromine, tetramethylammonium compounds, tetraethylammonium compounds, trimethylamine, triethylamine, tripropylamine and tributylamine and metal cations such as aluminum, calcium, copper, iron, lithium, magnesium, manganese, potassium, sodium, and zinc.

Pharmaceutically acceptable solvates illustratively include hydrates, ethanolates, methanolates.

Exemplary pharmaceutically acceptable amides include amides derived from ammonia, primary C1-C6 alkyl amines and secondary C1-C6 dialkyl amines including those in the form of a 5- or 6-member nitrogen-containing heterocycle.

A TIC10 prodrug is a form of TIC10 covalently bound to a moiety which is released from TIC10 yielding the intact active TIC10. Prodrug forms are well known in the art as exemplified in Sloan, K. B., Prodrugs, M. Dekker, New York, 1992; and Testa, B. and Mayer, J. M., Hydrolysis in drug and prodrug metabolism: chemistry, biochemistry, and enzymology, Wiley-VCH, Zurich, 2003.

Pharmaceutical compositions are provided which include:

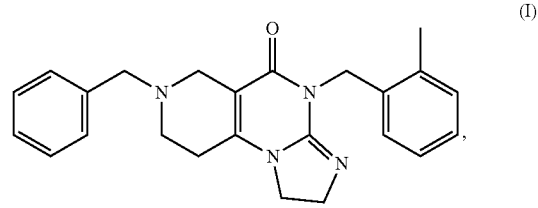 [SMILES: Cc1ccccc1CN1C(=O)C2=C(CCN(Cc3ccccc3)C2)N2CCN=C12]

(I)

a pharmaceutically acceptable derivative, salt, ester, amide, hydrate, solvate and/or prodrug thereof as a first therapeutic agent; a pharmaceutically acceptable carrier; and a second therapeutic agent, such as an anti-cancer agent.

Methods of treatment of a subject in need thereof are provided according to aspects of the present invention including administration of a pharmaceutically effective amount of:

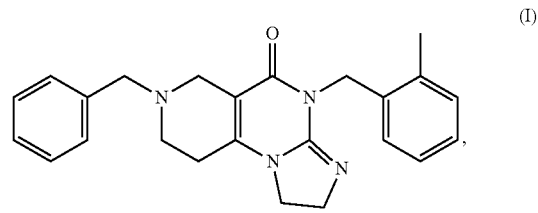 [SMILES: Cc1ccccc1CN1C(=O)C2=C(CCN(Cc3ccccc3)C2)N2CCN=C12]

(I)

a pharmaceutically acceptable derivative, salt, ester, amide, hydrate, solvate and/or prodrug thereof; and a pharmaceutically acceptable carrier.

Methods of treatment of a subject in need thereof are provided including administration of a pharmaceutically effective amount of

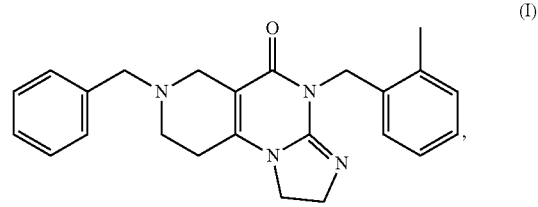 [SMILES: Cc1ccccc1CN1C(=O)C2=C(CCN(Cc3ccccc3)C2)N2CCN=C12]

(I)

a pharmaceutically acceptable derivative, salt, ester, amide, hydrate, solvate and/or prodrug thereof; and a pharmaceutically acceptable carrier; effective to induce expression of TRAIL in the subject.

TRAIL protein can be assayed in a test sample obtained from a subject to detect TIC10-induced TRAIL expression.

Immunoassay methods can be used to assay TRAIL in a sample, including, but not limited to, enzyme-linked immunosorbent assay (ELISA), enzyme-linked immunofiltration assay (ELIFA), flow cytometry, immunoblot, immunoprecipitation, immunohistochemistry, immunocytochemistry, luminescent immunoassay (LIA), fluorescent immunoassay (FIA), and radioimmunoassay. Assay methods may be used to obtain qualitative and/or quantitative results. Specific details of suitable assay methods for both qualitative and quantitative assay of a sample are described in standard references, illustratively including E. Harlow and D. Lane, Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; B. K. C. Lo, Antibody Engineering: Methods and Protocols, Methods in Molecular Biology, Humana Press, 2003; F. M. Ausubel et al., Eds., Short Protocols in Molecular Biology, Current Protocols, Wiley, 2002; S. Klussman, Ed., The Aptamer Handbook: Functional Oligonucleotides and Their Applications, Wiley, 2006; Ormerod, M. G., Flow Cytometry: a practical approach, Oxford University Press, 2000; Givan, A. L., Flow Cytometry: first principles, Wiley, New York, 2001; Gorczyca, W., Flow Cytometry in Neoplastic Hematology: morphologic-immunophenotypic correlation, Taylor & Francis, 2006; Crowther, J. R., The ELISA Guidebook (Methods in Molecular Biology), Humana Press, 2000; Wild, D., The Immunoassay Handbook, 3rd Edition, Elsevier Science, 2005. and J. Sambrook and D. W. Russell, Molecular Cloning: A Laboratory Manual, Cold Spring Harbor Laboratory Press, 3rd Ed., 2001.

Aptamers can be used to assay a sample for TRAIL. The term "aptamer" refers to a peptide and/or nucleic acid that substantially specifically binds to a specified substance. In the case of a nucleic acid aptamer, the aptamer is characterized by binding interaction with a target other than Watson/Crick base pairing or triple helix binding with a second and/or third nucleic acid. Such binding interaction may include Van der Waals interaction, hydrophobic interaction, hydrogen bonding and/or electrostatic interactions, for example. Similarly, peptide-based aptamers are characterized by specific binding to a target wherein the aptamer is not a naturally occurring ligand for the target. Techniques for identification and generation of peptide and nucleic acid aptamers and their use are known in the art as described, for example, in F. M. Ausubel et al., Eds., Short Protocols in Molecular Biology, Current Protocols, Wiley, 2002; S. Klussman, Ed., The Aptamer Handbook: Functional Oligonucleotides and Their Applications, Wiley, 2006; and J. Sambrook and D. W. Russell, Molecular Cloning: A Laboratory Manual, Cold Spring Harbor Laboratory Press, 3rd Ed., 2001.

Spectrometric analysis is used to assay a sample for TRAIL. For example mass analysis can be used in an assay according to aspects of the present invention. Mass analysis is conducted using, for example, time-of-flight (TOF) mass spectrometry or Fourier transform ion cyclotron resonance mass spectrometry. Mass spectrometry techniques are known in the art and exemplary detailed descriptions of methods for protein and/or peptide assay are found in Li J., et al., Clin Chem., 48(8):1296-304, 2002; Hortin, G. L., Clinical Chemistry 52: 1223-1237, 2006; Hortin, G. L., Clinical Chemistry 52: 1223-1237, 2006; A. L. Burlingame, et al. (Eds.), Mass Spectrometry in Biology and Medicine, Humana Press, 2000; and D. M. Desiderio, Mass Spectrometry of Peptides, CRC Press, 1990.

Localization of TRAIL at the surface of cells can be assayed to detect an effect of a pharmaceutical composition of the present invention. Detection of TRAIL localization can be performed by immunoassay, such as flow cytometry, as well as by immunohistochemistry.

A test sample can be any biological fluid, cell or tissue of a subject, illustratively including blood, plasma, serum, urine, saliva, ascites, cerebrospinal fluid, cerebroventricular fluid, pleural fluids, pulmonary and bronchial lavage samples, mucous, sweat, tears, semen, bladder wash samples, amniotic fluid, lymph, peritoneal fluid, synovial fluid, bone marrow aspirate, tumor cells or tissue, organ cells or tissue, such as biopsy material. In preferred aspects, a test sample is blood, plasma or serum.

A test sample from a subject is optionally purified for TRAIL or other biomarker assay. The term "purified" in the context of a test sample refers to separation of TRAIL or another biomarker from at least one other component present in the test sample. Test sample purification is achieved by techniques illustratively including electrophoretic methods such as gel electrophoresis and 2-D gel electrophoresis; chromatography methods such as HPLC, ion exchange chromatography, affinity chromatography, size exclusion chromatography, thin layer and paper chromatography.

Assay of TRAIL can be performed on cells and tissues. For example, immunohistochemical methods and in situ hybridization can be used to assay TRAIL protein and/or nucleic acid in a cell or tissue test sample.

One or more standards can be used to allow quantitative determination of TRAIL in a sample.

Assay of TRAIL in a test sample may be compared to assay of TRAIL in a control sample. Control samples may be obtained from one or more normal subjects, for example.

According to aspects of the present invention, assays for TRAIL are used to monitor a subject. Thus, for example, a test sample is obtained from the subject before treatment with a pharmaceutical composition of the present invention and at one or more times during and/or following treatment in order to assess effectiveness of the treatment. In a further example, a test sample is obtained from the subject at various times in order to assess the course or progress of disease or healing.

In particular aspects, one or more additional biomarkers are assayed in a test sample obtained from a subject to aid in monitoring treatment with a pharmaceutical composition of the present invention. For example, one or more of phospho-ERK, phospho-Akt, Foxo3a localization and/or phosphorylation is assayed in a test sample obtained from a subject to aid in monitoring treatment with a pharmaceutical composition of the present invention. Such additional biomarkers are assayed by immunoassay methods such those described herein.

TRAIL nucleic acid can be assayed in a test sample obtained from a subject to detect TIC10-induced TRAIL expression. Assays for detecting TRAIL nucleic acids, particularly mRNA or cDNA, include, but are not limited to, polymerase chain reactions (PCR) such as RT-PCR, dot blot, in situ hybridization, Northern blot and RNase protection.

Methods and compositions are provided according to the present invention for treating cancer.

Methods of treatment of a subject having, or at risk of having, cancer, are provided according to aspects of the present invention including administration of a pharmaceutically effective amount of

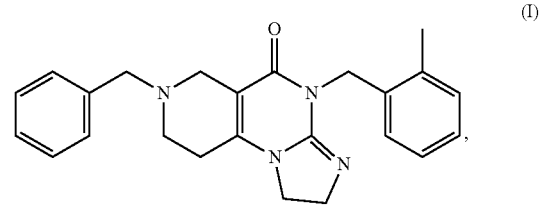 [SMILES: Cc1ccccc1CN1C(=O)C2=C(CCN(Cc3ccccc3)C2)N2CCN=C12]

a pharmaceutically acceptable derivative, salt, ester, amide, hydrate, solvate and/or prodrug thereof; and a pharmaceutically acceptable carrier.

Methods of treatment of a subject having, or at risk of having, cancer, are provided including administration of a pharmaceutically effective amount of

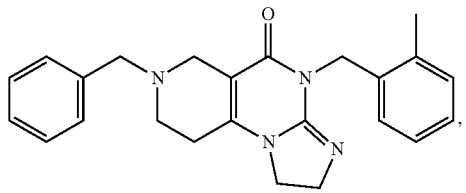

a pharmaceutically acceptable derivative, salt, ester, amide, hydrate, solvate and/or prodrug thereof; and a pharmaceutically acceptable carrier; effective to induce expression of TRAIL in the subject.

Cancers treated using methods and compositions described herein are characterized by abnormal cell proliferation including, but not limited to, pre-neoplastic hyperproliferation, cancer in-situ, neoplasms and metastasis. Methods and compositions of the present invention can be used for prophylaxis as well as amelioration of signs and/or symptoms of cancer. The terms "treating" and "treatment" used to refer to treatment of a cancer in a subject include: preventing, inhibiting or ameliorating the cancer in the subject, such as slowing progression of the cancer and/or reducing or ameliorating a sign or symptom of the cancer.

A pharmaceutically effective amount of a composition of the present invention is an amount which has a beneficial effect in a subject being treated. In subjects having cancer or at risk for having cancer, such as a condition characterized by abnormal cell proliferation including, but not limited to, pre-neoplastic hyperproliferation, cancer in-situ, neoplasms, metastasis, a tumor, a benign growth or other condition responsive to a composition of the present invention, a pharmaceutically effective amount of a composition of the present invention is effective to ameliorate or prevent one or more signs and/or symptoms of the condition. For example, a pharmaceutically effective amount of a composition of the present invention is effective to detectably increase apoptosis and/or decrease proliferation of cells of a cancer condition characterized by abnormal cell proliferation including, but not limited to, pre-neoplastic hyperproliferation, cancer in-situ, neoplasms, metastasis, a tumor, a benign growth or other condition responsive to a composition of the present invention.

TIC10 possesses broad-spectrum activity described herein in primary patient samples and cell lines that are resistant to conventional therapies, indicative that the therapeutic action of TIC10 does not rely exclusively on commonly altered molecules in cancer such as EGFR, Her2, KRAS, or PTEN. The elucidation of the therapeutic cellular mechanism of TIC10 allows for the identification of resistance mechanisms such as over-activated Akt, described herein, and provides phospho-ERK, phospho-Akt, Foxo3a localization and phosphorylation, and surface and serum TRAIL as correlative biomarkers of TIC10 therapeutic activity in cancer.

Thus, according to aspects of the present invention, one or more correlative biomarkers of TIC10 therapeutic activity in cancer are assayed to assess treatment with a pharmaceutical composition of the present invention.

A subject treated according to methods and using compositions of the present invention can be mammalian or non-mammalian. A mammalian subject can be any mammal including, but not limited to, a human; a non-human primate; a rodent such as a mouse, rat, or guinea pig; a domesticated pet such as a cat or dog; a horse, cow, pig, sheep, goat, or rabbit. A non-mammalian subject can be any non-mammal including, but not limited to, a bird such as a duck, goose, chicken, or turkey. Subjects can be either gender and can be any age. In aspects of methods including administration of an inventive pharmaceutical composition to a subject, the subject is human. The terms "subject" and "patient" are used interchangeably herein.

A pharmaceutical composition according to the invention generally includes about 0.1-99% of TIC10, a pharmaceutically acceptable derivative, salt, ester, amide, hydrate, solvate and/or prodrug thereof; and a pharmaceutically acceptable carrier. Combinations of TIC10 and at least one pharmaceutically acceptable derivative, salt, ester, amide, hydrate, solvate and/or prodrug thereof in a pharmaceutical composition are also considered within the scope of the present invention. Furthermore, combinations of at least two of: a pharmaceutically acceptable derivative, salt, ester, amide, hydrate, solvate and prodrug thereof in a pharmaceutical composition, are also considered within the scope of the present invention.

Combinations of therapeutic agents are administered according to aspects of the present invention. According to aspects, of the present invention methods of treatment of cancer in a subject include administration of a pharmaceutical composition of TIC10, a pharmaceutically acceptable derivative, salt, ester, amide, hydrate, solvate and/or prodrug thereof; and at least one additional therapeutic agent. According to aspects, of the present invention methods of treatment of cancer in a subject include administration of a pharmaceutical composition of TIC10, a pharmaceutically acceptable derivative, salt, ester, amide, hydrate, solvate and/or prodrug thereof; and at least two additional therapeutic agents.

The term "additional therapeutic agent" is used herein to refer to a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues which is a biologically, physiologically, or pharmacologically active substance (or substances) that acts locally or systemically in a subject.

Additional therapeutic agents included according to aspects of methods and compositions of the present invention include, but are not limited to, antibiotics, antivirals, antineoplastic agents, analgesics, antipyretics, antidepressants, antipsychotics, anti-cancer agents, antihistamines, anti-osteoporosis agents, anti-osteonecrosis agents, antiinflammatory agents, anxiolytics, chemotherapeutic agents, diuretics, growth factors, hormones, non-steroidal anti-inflammatory agents, steroids and vasoactive agents.

Combination therapies utilizing TIC10, a pharmaceutically acceptable derivative, salt, ester, amide, hydrate, solvate and/or prodrug thereof and one or more additional therapeutic agents may show synergistic effects, e.g., a greater therapeutic effect than would be observed using a pharmaceutical composition of the present invention including TIC10, a pharmaceutically acceptable derivative, salt, ester, amide, hydrate, solvate and/or prodrug thereof, or one or more additional therapeutic agents alone as a monotherapy.

According to aspects, combination therapies include: (1) pharmaceutical compositions that include a pharmaceutical composition including TIC10, a pharmaceutically acceptable derivative, salt, ester, amide, hydrate, solvate and/or prodrug thereof of the present invention formulated together in a single composition with one or more additional therapeutic agents; and (2) co-administration of a pharmaceutical composition including TIC10, a pharmaceutically acceptable derivative, salt, ester, amide, hydrate, solvate and/or prodrug thereof of the present invention with one or more additional therapeutic agents wherein the pharmaceutical composition including TIC10, a pharmaceutically acceptable derivative, salt, ester, amide, hydrate, solvate and/or prodrug thereof of the present invention and the one or more additional therapeutic agents have not been formulated in the same composition. When using separate formulations, the pharmaceutical composition including TIC10, a pharmaceutically acceptable derivative, salt, ester, amide, hydrate, solvate and/or prodrug thereof of the present invention may be administered at the same time, intermittent times, staggered times, prior to, subsequent to, or combinations thereof, with reference to the administration of the one or more additional therapeutic agents.

Combination treatments can allow for reduced effective dosage and increased therapeutic index of the pharmaceutical composition including TIC10, a pharmaceutically acceptable derivative, salt, ester, amide, hydrate, solvate and/or prodrug thereof of the present invention and the one or more additional therapeutic agents used in methods of the present invention.

According to aspects, combination therapies include: (1) pharmaceutical compositions that include a pharmaceutical composition including TIC10, a pharmaceutically acceptable derivative, salt, ester, amide, hydrate, solvate and/or prodrug thereof of the present invention formulated together in a single composition with one or more additional anti-cancer agents; and (2) co-administration of a pharmaceutical composition including TIC10, a pharmaceutically acceptable derivative, salt, ester, amide, hydrate, solvate and/or prodrug thereof of the present invention with one or more additional anti-cancer agents wherein the pharmaceutical composition including TIC10, a pharmaceutically acceptable derivative, salt, ester, amide, hydrate, solvate and/or prodrug thereof of the present invention and the one or more additional therapeutic agents have not been formulated in the same composition. When using separate formulations, the pharmaceutical composition including TIC10, a pharmaceutically acceptable derivative, salt, ester, amide, hydrate, solvate and/or prodrug thereof of the present invention may be administered at the same time, intermittent times, staggered times, prior to, subsequent to, or combinations thereof, with reference to the administration of the one or more additional anti-cancer agents.

Anti-cancer agents are described, for example, in Goodman et al., Goodman and Gilman's The Pharmacological Basis of Therapeutics, 8th Ed., Macmillan Publishing Co., 1990.

Anti-cancer agents illustratively include acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bevacizumab, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, dromostanolone, duazomycin, edatrexate, eflornithine, elsamitrucin, enloplatin, enpromate, epipropidine, epirubicin, erbulozole, esorubicin, estramustine, etanidazole, etoposide, etoprine, fadrozole, fazarabine, fenretinide, floxuridine, fludarabine, fluorouracil, flurocitabine, fosquidone, fostriecin, fulvestrant, gemcitabine, hydroxyurea, idarubicin, ifosfamide, ilmofosine, interleukin II (IL-2, including recombinant interleukin II or rIL2), interferon alfa-2a, interferon alfa-2b, interferon alfa-n1, interferon alfa-n3, interferon beta-Ia, interferon gamma-Ib, iproplatin, irinotecan, lanreotide, letrozole, leuprolide, liarozole, lometrexol, lomustine, losoxantrone, masoprocol, maytansine, mechlorethamine hydrochlride, megestrol, melengestrol acetate, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, pyrazofurin, riboprine, rogletimide, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, verteporfin, vinblastine, vincristine sulfate, vindesine, vinepidine, vinglycinate, vinleurosine, vinorelbine, vinrosidine, vinzolidine, vorozole, zeniplatin, zinostatin, zoledronate, and zorubicin.

Synergistic effects of combination treatment with a pharmaceutical composition including TIC10 with one or more additional anti-cancer agents such as one or more mitotic inhibitors and/or one or more anti-angiogenic agents is unexpectedly found as described herein.

According to aspects of the present invention, a method of treating a subject having cancer or at risk of having cancer includes administration of a therapeutically effective amount of TIC10, a pharmaceutically acceptable derivative, salt, ester, amide, hydrate, solvate and/or prodrug thereof; and a mitotic inhibitor.

According to aspects of the present invention, a method of treating a subject having cancer or at risk of having cancer includes administration of a therapeutically effective amount of TIC10, a pharmaceutically acceptable derivative, salt, ester, amide, hydrate, solvate and/or prodrug thereof; and a taxane mitotic inhibitor, such as, but not limited to, paclitaxel and docetaxel.

According to aspects of the present invention, a method of treating a subject having cancer or at risk of having cancer includes administration of a therapeutically effective amount of TIC10, a pharmaceutically acceptable derivative, salt, ester, amide, hydrate, solvate and/or prodrug thereof; and an anti-angiogenic agent.

According to aspects of the present invention, a method of treating a subject having cancer or at risk of having cancer includes administration of a therapeutically effective amount of TIC10, a pharmaceutically acceptable derivative, salt, ester, amide, hydrate, solvate and/or prodrug thereof; and an anti-angiogenic agent, such as, but not limited to, bevacizumab.

In particular aspects of inventive compositions, the amount of the adjunct anti-cancer agent administered is less than an amount of the adjunct anti-cancer agent necessary to achieve a therapeutic effect if administered without administration of a therapeutically effective amount of structure (I), a pharmaceutically acceptable derivative, salt, ester, amide, hydrate, solvate and/or prodrug thereof. Thus, in particular aspects of compositions of the present invention, the amount of the adjunct anti-cancer agent in a unit dose of the composition is at least 5%, at least 10%, at least 15%, at least 20%, at least 25%, at least 30%, at least 35%, at least 40%, at least 50%, at least 55%, at least 60%, at least 65%, at least 70%, at least 75%, at least 80%, at least 85%, or at least 90%, less than an amount of the adjunct anti-cancer agent necessary to achieve a therapeutic effect if administered without the therapeutically effective amount of structure (I), a pharmaceutically acceptable derivative, salt, ester, amide, hydrate, solvate and/or prodrug thereof.

According to aspects of the present invention, TRAIL can be induced or provided by methods or compositions in addition to administration of TIC10, such as by administration of one or more histone deacetylase (HDAC) inhibitors such as vorinostat, described in Nebbioso, A. et al, 2005, Nat Med 11, 77-84; one or more TRAIL-agonist antibodies such as lexatumumab and mapatumumab; and/or recombinant TRAIL such as adenoviral TRAIL as described in Abdulghani, J. et al., 2010, Exp. Opin. Ther. Targets 14:1091-1108.

Optionally, a method of treating a subject having cancer or at risk of having cancer further includes an adjunct anti-cancer treatment. An adjunct anti-cancer treatment can be a radiation treatment of a subject or an affected area of a subject's body.

TRAIL expression induced in the subject by administration of a pharmaceutical composition of the present invention is detectable in a sample obtained from the subject, such as a blood sample obtained from the subject.

Aspects of the present invention include upregulation of the TRAIL gene by normal and tumor tissues with sustained serum levels of secreted TRAIL, after a single dose of TIC10, for 3-4 days. Normally the serum half-life of the TRAIL protein is 20-30 minutes.

TIC10 has a calculated mass of 387.21 and crosses the blood-brain barrier. Administration of TIC10 allows for induction of TRAIL in cells of the central nervous system, illustratively including glial cells and neurons of the brain and spinal cord. Further, administration of a pharmaceutically acceptable derivative, salt, ester, amide, hydrate, solvate or prodrug of TIC10 which crosses the blood-brain barrier allows for induction of TRAIL in cells of the central nervous system.

Methods of treatment of a subject having, or at risk of having, a central nervous system (CNS) cancer are provided according to aspects of the present invention which include administration of a pharmaceutically effective amount of:

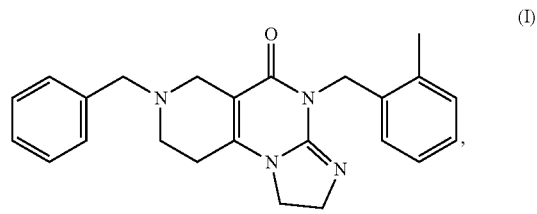 [SMILES: Cc1ccccc1CN1C(=O)C2=C(CCN(Cc3ccccc3)C2)N2CCN=C12]
(I)

a pharmaceutically acceptable derivative, salt, ester, amide, hydrate, solvate and/or prodrug thereof; and a pharmaceutically acceptable carrier by a route of administration other than by direct administration to the CNS.

Primary CNS cancers and CNS metastases of non-CNS cancers, also called brain cancer herein, are treated according to aspects of the present invention. Primary CNS cancers treated according to aspects of the present invention include but are not limited to gliomas, meningiomas, pituitary adenomas and nerve sheath tumors. Glioblastoma multiforme is a primary CNS cancer treated according to aspects of the present invention. Oligodendrogliomas are primary CNS cancers treated according to aspects of the present invention.

Methods of the present invention include administration of a pharmaceutical composition of the present invention by a route of administration including, but not limited to, oral, rectal, nasal, pulmonary, epidural, ocular, otic, intraarterial, intracardiac, intracerebroventricular, intradermal, intravenous, intramuscular, intraperitoneal, intraosseous, intrathecal, intravesical, subcutaneous, topical, transdermal, and transmucosal, such as by sublingual, buccal, vaginal, and inhalational, routes of administration.

Methods of treatment of a subject in need thereof are provided according to aspects of the present invention which include oral administration of a pharmaceutically effective amount of:

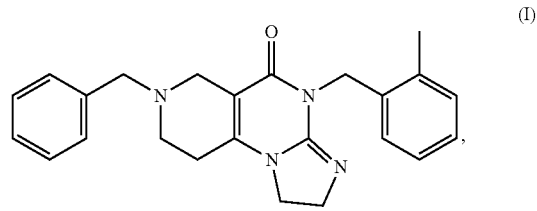 [SMILES: Cc1ccccc1CN1C(=O)C2=C(CCN(Cc3ccccc3)C2)N2CCN=C12]
(I)

a pharmaceutically acceptable derivative, salt, ester, amide, hydrate, solvate and/or prodrug thereof, formulated for oral administration.

A pharmaceutical composition of the present invention may be in any dosage form suitable for administration to a subject, illustratively including solid, semi-solid and liquid dosage forms such as tablets, capsules, powders, granules, suppositories, pills, solutions, suspensions, ointments, lotions, creams, gels, pastes, sprays and aerosols. Liposomes and emulsions are well-known types of pharmaceutical formulations that can be used to deliver a pharmaceutical agent, particularly a hydrophobic pharmaceutical agent. Pharmaceutical compositions of the present invention generally include a pharmaceutically acceptable carrier such as an excipient, diluent and/or vehicle. Delayed release formulations of compositions and delayed release systems, such as semipermeable matrices of solid hydrophobic polymers can be used.

A pharmaceutical formulation of a composition of the present invention can include a pharmaceutically acceptable carrier. The term "pharmaceutically acceptable carrier" refers to a carrier which is suitable for use in a subject without undue toxicity or irritation to the subject and which is compatible with other ingredients included in a pharmaceutical composition.

Pharmaceutically acceptable carriers, methods for making pharmaceutical compositions and various dosage forms, as well as modes of administration are well-known in the art, for example as detailed in Pharmaceutical Dosage Forms: Tablets, eds. H. A. Lieberman et al., New York: Marcel Dekker, Inc., 1989; and in L. V. Allen, Jr. et al., Ansel's Pharmaceutical Dosage Forms and Drug Delivery Systems, 8th Ed., Philadelphia, Pa.: Lippincott, Williams & Wilkins, 2004; A. R. Gennaro, Remington: The Science and Practice of Pharmacy, Lippincott Williams & Wilkins, 21st ed., 2005, particularly chapter 89; and J. G. Hardman et al., Goodman & Gilman's The Pharmacological Basis of Therapeutics, McGraw-Hill Professional, 10th ed., 2001.

Pharmaceutical compositions according to aspects of the present invention are formulated for oral administration.

A solid dosage form for administration or for suspension in a liquid prior to administration illustratively includes capsules, tablets, powders, and granules. In such solid dosage forms, one or more active agents, is admixed with at least one carrier illustratively including a buffer such as, for example, sodium citrate or an alkali metal phosphate illustratively including sodium phosphates, potassium phosphates and calcium phosphates; a filler such as, for example, starch, lactose, sucrose, glucose, mannitol, and silicic acid; a binder such as, for example, carboxymethylcellulose, alignates, gelatin, polyvinylpyrrolidone, sucrose, and *acacia*; a humectant such as, for example, glycerol; a disintegrating agent such as, for example, agar-agar, calcium carbonate, plant starches such as potato or tapioca starch, alginic acid, certain complex silicates, and sodium carbonate; a solution retarder such as, for example, paraffin; an absorption accelerator such as, for example, a quaternary ammonium compound; a wetting agent such as, for example, cetyl alcohol, glycerol monostearate, and a glycol; an adsorbent such as, for example, kaolin and bentonite; a lubricant such as, for example, talc, calcium stearate, magnesium stearate, a solid polyethylene glycol or sodium lauryl sulfate; a preservative such as an antibacterial agent and an antifungal agent, including for example, sorbic acid, gentamycin and phenol; and a stabilizer such as, for example, sucrose, EDTA, EGTA, and an antioxidant.

Solid dosage forms optionally include a coating such as an enteric coating. The enteric coating is typically a polymeric material. Preferred enteric coating materials have the characteristics of being bioerodible, gradually hydrolyzable and/or gradually water-soluble polymers. The amount of coating material applied to a solid dosage generally dictates the time interval between ingestion and drug release. A coating is applied having a thickness such that the entire coating does not dissolve in the gastrointestinal fluids at pH below 3 associated with stomach acids, yet dissolves above pH 3 in the small intestine environment. It is expected that any anionic polymer exhibiting a pH-dependent solubility profile is readily used as an enteric coating in the practice of the present invention to achieve delivery of the active agent to the lower gastrointestinal tract. The selection of the specific enteric coating material depends on properties such as resistance to disintegration in the stomach; impermeability to gastric fluids and active agent diffusion while in the stomach; ability to dissipate at the target intestine site; physical and chemical stability during storage; non-toxicity; and ease of application.

Suitable enteric coating materials illustratively include cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonium methylacrylate, ethyl acrylate, methyl methacrylate and/or ethyl; vinyl polymers and copolymers such as polyvinyl pyrrolidone, polyvinyl acetate, polyvinylacetate phthalate, vinylacetate crotonic acid copolymer, and ethylene-vinyl acetate copolymers; shellac; and combinations thereof. A particular enteric coating material includes acrylic acid polymers and copolymers described for example U.S. Pat. No. 6,136,345.

The enteric coating optionally contains a plasticizer to prevent the formation of pores and cracks that allow the penetration of the gastric fluids into the solid dosage form. Suitable plasticizers illustratively include, triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, a coating composed of an anionic carboxylic acrylic polymer typically contains approximately 10% to 25% by weight of a plasticizer, particularly dibutyl phthalate, polyethylene glycol, triethyl citrate and triacetin. The coating can also contain other coating excipients such as detackifiers, antifoaming agents, lubricants (e.g., magnesium stearate), and stabilizers (e.g. hydroxypropylcellulose, acids or bases) to solubilize or disperse the coating material, and to improve coating performance and the coated product.

Liquid dosage forms for oral administration include one or more active agents and a pharmaceutically acceptable carrier formulated as an emulsion, solution, suspension, syrup, or elixir. A liquid dosage form of a composition of the present invention may include a colorant, a stabilizer, a wetting agent, an emulsifying agent, a suspending agent, a sweetener, a flavoring, or a perfuming agent.

For example, a composition for parenteral administration may be formulated as an injectable liquid. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of a desirable particle size in the case of dispersions, and/or by the use of a surfactant, such as sodium lauryl sulfate. A stabilizer is optionally included such as, for example, sucrose, EDTA, EGTA, and an antioxidant.

For topical administration, a composition can be formulated for administration to the skin such as for local effect, and/or as a "patch" formulation for transdermal delivery. Pharmaceutical formulations suitable for topical administration include, for example, ointments, lotions, creams, gels, pastes, sprays and powders. Ointments, lotions, creams, gels and pastes can include, in addition to one or more active agents, a base such as an absorption base, water-removable base, water-soluble base or oleaginous base and excipients such as a thickening agent, a gelling agent, a colorant, a stabilizer, an emulsifying agent, a suspending agent, a sweetener, a flavoring, or a perfuming agent.

Transdermal formulations can include percutaneous absorption enhancers such as acetone, azone, dimethyl acetamide, dimethyl formamide, dimethyl sulfoxide, ethanol, oleic acid, polyethylene glycol, propylene glycol and sodium lauryl sulfate. Iontophoresis and/or sonophoresis can be used to enhance transdermal delivery.

Powders and sprays for topical administration of one or more active agents can include excipients such as talc, lactose and one or more silicic acids. Sprays can include a pharmaceutical propellant such as a fluorinated hydrocarbon propellant, carbon dioxide, or a suitable gas. Alternatively, a spray can be delivered from a pump-style spray device which does not require a propellant. A spray device delivers a metered dose of a composition contained therein, for example, using a valve for regulation of a delivered amount.

Opthalmic formulations of one or more active agents can include ingredients such as a preservative, a buffer and a thickening agent.

Suitable surface-active agents useful as a pharmaceutically acceptable carrier or excipient in the pharmaceutical compositions of the present invention include non-ionic, cationic and/or anionic surfactants having good emulsifying, dispersing and/or wetting properties. Suitable anionic surfactants include both water-soluble soaps and water-soluble synthetic surface-active agents. Suitable soaps are alkaline or alkaline-earth metal salts, non-substituted or substituted ammonium salts of higher fatty acids (C10-C22), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, non-substituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphtalenesulphonic acid or a naphtalenesulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidylcholine, dipalmitoylphoshatidyl-choline and their mixtures.

Suitable non-ionic surfactants useful as pharmaceutically acceptable carriers or excipients in the pharmaceutical compositions of the present invention include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants useful as pharmaceutically acceptable carriers or excipients in the pharmaceutical compositions of the present invention include quaternary ammonium salts, preferably halides, having 4 hydrocarbon radicals optionally substituted with halo, phenyl, substituted phenyl or hydroxy; for instance quaternary ammonium salts containing as N-substituent at least one C8-C22 alkyl radical (e.g. cetyl, lauryl, palmityl, myristyl, oleyl and the like) and, as further sub-stituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbuch", 2nd ed. (Hanser Verlag, Vienna, 1981) and "Encyclopaedia of Surfactants (Chemical Publishing Co., New York, 1981).

Structure-forming, thickening or gel-forming agents may be included into the pharmaceutical compositions and combined preparations of the invention. Suitable such agents are in particular highly dispersed silicic acid, such as the product commercially available under the trade name Aerosil; bentonites; tetraalkyl ammonium salts of montmorillonites (e.g., products commercially available under the trade name Bentone), wherein each of the alkyl groups may contain from 1 to 20 carbon atoms; cetostearyl alcohol and modified castor oil products (e.g. the product commercially available under the trade name Antisettle).

In particular aspects, a pharmaceutically acceptable carrier is a particulate carrier such as lipid particles including liposomes, micelles, unilamellar or mulitlamellar vesicles; polymer particles such as hydrogel particles, polyglycolic acid particles or polylactic acid particles; inorganic particles such as calcium phosphate particles such as described in for example U.S. Pat. No. 5,648,097; and inorganic/organic particulate carriers such as described for example in U.S. Pat. No. 6,630,486.

A particulate pharmaceutically acceptable carrier can be selected from among a lipid particle; a polymer particle; an inorganic particle; and an inorganic/organic particle. A mixture of particle types can also be included as a particulate pharmaceutically acceptable carrier.

A particulate carrier is typically formulated such that particles have an average particle size in the range of about 1 nm-10 microns. In particular aspects, a particulate carrier is formulated such that particles have an average particle size in the range of about 1 nm-100 nm.

The dosage of an inventive pharmaceutical composition will vary based on factors such as, but not limited to, the route of administration; the age, health, sex, and weight of the subject to whom the composition is to be administered; the nature and extent of the subject's symptoms, if any, and the effect desired. Dosage may be adjusted depending on whether treatment is to be acute or continuing. One of skill in the art can determine a pharmaceutically effective amount in view of these and other considerations typical in medical practice.

In general it is contemplated that a daily dosage of an inventive pharmaceutical composition is in the range of about 0.001 to 100 milligrams per kilogram of a subject's body weight. A daily dose may be administered as two or more divided doses to obtain the desired effect. An inventive pharmaceutical composition may also be formulated for sustained release to obtain desired results.

Detailed information concerning customary ingredients, equipment and processes for preparing dosage forms is found in Pharmaceutical Dosage Forms: Tablets, eds. H. A. Lieberman et al., New York: Marcel Dekker, Inc., 1989; and in L. V. Allen, Jr. et al., Ansel's Pharmaceutical Dosage Forms and Drug Delivery Systems, 8th Ed., Philadelphia, Pa.: Lippincott, Williams & Wilkins, 2004; A. R. Gennaro, Remington: The Science and Practice of Pharmacy, Lippincott Williams & Wilkins, 21st ed., 2005, particularly chapter 89; and J. G. Hardman et al., Goodman & Gilman's The Pharmacological Basis of Therapeutics, McGraw-Hill Professional, 10th ed., 2001.

Commercial packages according to aspects of the present invention include a pharmaceutical composition described herein. Instructions for administering the pharmaceutical composition are included according to aspects of the invention.

According to aspects of the present invention, a commercial package includes

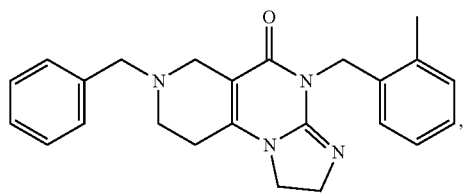

(I)

a pharmaceutically acceptable pharmaceutically acceptable derivative, salt, ester, amide, hydrate, solvate and/or prodrug thereof; and a pharmaceutically acceptable carrier.

One or more ancillary components is optionally included in commercial packages of the present invention, such as a buffer or diluent.

Aspects of inventive compositions and methods are illustrated in the following examples. These examples are provided for illustrative purposes and are not considered limitations on the scope of inventive compositions and methods.

Examples

Reagents and Cell-Based Assays

All cell lines were obtained from ATCC except HCT116 Bax$^{-/-}$ and HCT116 p53$^{-/-}$ cells obtained from Bert Vogelstein (Johns Hopkins University, Baltimore, Mass.) and GBM cell lines obtained from Akiva Mintz (Wake Forrest University, Winston-Salem, N.C.). Lentiviral infection was carried out with MDA-MB-231 cells using TRAIL shRNA or vector and HCT116 using Foxo3a shRNA or vector purchased from Sigma-Aldrich (St. Louis, Mo.). H460 DR5ΔDD-EGFP cells were constructed using cDNA coding for a DR5 fragment without death domain by inserting amino acids 1 to 298 of the human DR5 gene into the pEGFP-N1 vector to express a DR5(1-298)-fusion protein. The fusion construct was transfected into H460 cells with Lipofectamine 2000 (Invitrogen) and selected with G418. Positive clones were verified by florescence microscopy and Western blot analysis. Bioluminescent high-throughput screening using the NCI diversity set II was carried out in HCT116 Bax$^{-/-}$ cells that were stably cotransfected to express a firefly luciferase construct under transcriptional control of the first 504 base pairs of the TRAIL promoter upstream of the start of transcription of the human TRAIL gene. Compounds were tested at a working concentration of 20 nM, 200 nM, 500 nM, and 1 µM with bioluminescent assessment of transcriptional activity at 12, 24, 36, and 48 hours post-treatment. Details of the screening methodology are described in Wang et al., 2006, PNAS 103:11003-11008). TIC10 (NSC350625) was obtained from the NCI DTP, reconstituted in DMSO at 20 mM, aliquoted and stored at −20° C. A6730 and U0126 monoethanolate were obtained from Sigma. Purified, recombinant TRAIL was produced as described in Kim et al., 2004, J. of Biol. Chem. 279:40044-40052. The RIK-2 antibody (Santa-Cruz Biotechnology) was used at 1 µg/mL and zVAD-fmk (Promega) was used at 20 µM.

Primary Specimens from Human Patients

All primary specimens from human patients were received immediately following resection, manually digested in complete DMEM, filtered with a 100-µm nylon mesh, and plated at 2×10$^5$ cells/mL in complete DMEM for use in Examples described herein.

Mice

For subcutaneous xenografts, 4-6 week old female, athymic nu/nu mice (Charles River Laboratories) were inoculated with 1×10$^6$ cells (2.5×10$^6$ for T98G) of indicated cell lines in each rear flank as a 200 µL suspension of 1:1 Matrigel (BD):PBS. All intraperitoneal and intravenous injections were given at a total volume of 200 µL. Oral formulations of TIC10 were administered using an oral gavage and given as a 200 µL suspension containing 20% Cremophor EL® (Sigma), 10% DMSO, and 70% PBS. Tumors were monitored using digital calipers at indicated time points. All subcutaneous tumors were allowed to establish for 1-4 weeks post-injection until reaching a volume of ~125 mm$^3$ before treatment initiation. Relief of tumor burden was monitored for 3 weeks following disappearance of the tumor and confirmed by visual inspection after euthanasia.

Intracecal implantation was performed as described in Cespedes, M. V., et al., Am J Pathol, 2007, 170(3): p. 1077-1085.

For intracranial xenografts, anesthetized athymic nude mice were implanted with 2×10$^5$ SF767 cells in a 25 µL suspension of serum- and antibiotic-free RPMI. The site of injection was a burr hole created 1 mm lateral to the midline of the skull and 1 mm anterior to the coronal suture. The injection was gradually administered over 5 minutes with a Hamilton syringe and the burr hole was sealed using bone wax. Tumor take was assessed by bioluminescent imaging 2 weeks following implantation. Bioluminescent imaging of tumors was carried out on an IVIS imaging system as described in Wang et al., 2003, PNAS 100:15095-15100.

Near-infrared imaging of mice was carried out on a Pearl Impulse imaging system (LI-COR) following tail-vein injection of AngioSense® 680 (VisEn Medical, Woburn, Mass.) according to the manufacturer's protocols. 6 week old Eµ-myc mice were obtained from The Jackson Laboratory (B6.Cg-Tg(IghMyc)22Bri/J).

For CBC/differential and serum chemistry assays, 1 mL of blood was harvested from anesthetized mice by terminal cardiac puncture of the left ventricle. For serum chemistry, 500 µL was placed into a microfuge tube and allowed to clot for 30 minutes at room temperature followed by centrifugation. Serum was removed, centrifuged again to remove any further clots, and serum was submitted for analysis. For CBC/differentials, 500 μL of blood was collected into EDTA tubes and analyzed.

Statistical Analyses.

For pair-wise comparisons, data were analyzed by the Student's two-tailed t test using Excel (Microsoft). Log-rank statistical analysis was performed using a web-based script that interfaces with the statistical package R.

RT-qPCR

Total RNA was extracted using RNeasy Minikit (Qiagen) by following the manufacturer's instructions. cDNA was generated using SuperScript II (Invitrogen) with 1 μg of RNA and oligodT. Primers were: TRAIL forward (CAGAG-GAAGAAGCAACACATT, SEQ ID NO:1), TRAIL reverse (GGTTGATGATTCCCAGGAGTTTATTTTG, SEQ ID NO:2), GAPDH forward (CCACATCGCTCAGACACCAT, SEQ ID NO:3), GAPDH reverse (GGCAACAATATC-CACTTTACCAGAGT, SEQ ID NO:4). PCR amplification was performed with the Applied Biosystems 7900HT Fast Real-time Detection System. Samples were standardized to 10 ng/μl and twenty ng of cDNA per sample was then utilized as a template for real-time PCR using a SYBR Green Master Mix (Qiagen Corp, USA). Samples were normalized to GAPDH used under identical conditions. Quantitation used the 2ΔΔCt method of crossing thresholds described in Livak et al., 2001, Methods. 2001 December; 25(4):402-8, with GAPDH as the endogenous control for normalization. Reactions were performed in 384 well optical plates in a 7900HT instrument (Applied Biosystems), with 10 ul reaction volumes. Data analysis used the ABI PRISM 7900 Sequence Detection System 2.2 software. To exclude the possibility of genomic DNA contamination, control PCR reactions with no cDNA template and No-RT control samples were also performed for each gene-specific primer set. Quadruplicates of each PCR reaction were performed and the resultant data was averaged.

Immunofluorescence

Indicated cell lines were propagated in log-phase growth in six-well plates in the presence of absence of TIC10 at indicated working concentrations for 72 hr. Cells were fixed and permeabilized using Cytofix/Cytoperm solution (BD Biosciences, San Jose, Calif.) solution. Cells were incubated with anti-TRAIL (ab2435, Abcam, Cambridge, Mass.) at 1:100 or anti-active caspase-3 (559565, BD Pharmingen, San Diego, Calif.) at 1:250 in Perm/Wash solution (BD Biosciences) for 1 hr in the absence of light. Anti-rabbit Alexa Fluor 488 was incubated at 1:200 in Perm/Wash solution for 20 min at room temperature and rinsed in PBS. Hoechst 33342 (Invitrogen) was used as a nuclear counterstain according to the manufacturer's protocol. Fluorescence imaging was performed on an Axiovert inverted microscope (Carl Zeiss MicroImaging) using an iVision imaging system (Biovision).

Flow Cytometry and Cell Death Assays

For all flow cytometry analyses, floating and adherent cells were analyzed on a Coulter-Beckman Elite Epics cytometer. For surface TRAIL experiments, adherent cells were harvested by brief trypsinization, fixed in 4% paraformaldehyde in PBS for 20 min, incubated with an anti-TRAIL antibody for 2 hr (Abcam), washed and incubated with anti-rabbit Alexafluor 488 (Invitrogen) for 30 min, and analyzed. Cells were gated on forward and side scatter to eliminate debris and dead cells from the analysis. Surface TRAIL data is expressed as median fluorescence intensity relative to that of control samples unless indicated as otherwise. For Sub-G1 and cell cycle profile experiments, all cells were pelleted and ethanol fixed followed by staining with propidium iodide (Sigma) in the presence of RNAse. Cell viability assays were carried out in 96-well black-walled clear-bottom plates using CellTiter-Glo® (Promega) according to the manufacturer's protocols. Imaging and quantification of these assays were performed on an IVIS imaging system (Xenogen).

Colony Formation Assays

Indicated cell lines were plated at 500 cells per well and treated the following day in fresh complete media after adherence. At 3 days post-treatment, the media was replaced with drug-free media and cells were propagated for 10 days with fresh media given once every 3 days. At the end of the 10 day period, cells were washed in PBS, fixed with methanol, and stained with Coomassie blue, rinsed, and dried for quantification.

Tissue Analyses.

Mice were humanely sacrificed at indicated time points and excised normal tissue or tumors were fixed in 4% paraformaldehyde/PBS overnight at 4° C. If plasma samples were desired, 500 μL of blood was collected by terminal cardiac puncture under anesthesia in EDTA-Vacutainer tubes (BD). Serum samples were collected in a similar fashion but in microcentrifuge tubes followed by a 30 minute incubation at room temperature to allow for clotting. Serum was then removed following centrifugation for 5 minutes. Paraffin-embedded blocks, serial section slides, and hematoxylin and eosin staining were prepared according to standard procedures. TUNEL staining was performed using the ApopTag® Peroxidase In Situ Apoptosis Detection Kit (Millipore). For IHC analysis, slides were dewaxed in xylene and hydrated in a decreasing gradient of ethanol. Antigen retrieval was carried out by boiling in 10 mM citric acid (pH 6.0) for 6 min. Samples were blocked with streptavidin and biotin blocking solutions and goat serum (Vector Laboratories). Primary antibodies were incubated overnight at 4° C. in a humidity chamber. Incubation with biotinylated secondary antibody and DAB deposition was carried out according the manufacturer's protocol (Vector Laboratories DAB Substrate Kit for Peroxidase). Samples were counterstained with hematoxylin (DAKO) for 6 min, rinsed in dH$_2$O for 5 min, rinsed with PBS, and dehydrated and sealed under cover slips. Images were recorded on an Axioskop microscope using QCapture software (QImaging).

Co-Cultures

Co-cultures of HCT116 p53$^{-/-}$ and HFF cells were performed in a 1:1 mixture of complete DMEM and McCoy's 5A medium. For fluorescence images, the two cells were separately labeled using the Fluorescent Cell Linkers Kits for gene cell membrane labeling (Sigma) according to the manufacturer's protocols. Cells were counterstained with Hoechst 33342 as described in the immunofluorescence section. For flow cytometry analysis of cell death, the two populations of cells were determined by differential light scattering and analyzed as described for sub-G1 analysis in the cell death assays section.

ELISA

ELISA for TRAIL was carried out using the Quantikine® TRAIL/TNFSF10 kit according to the manufacturer's protocol (DTRL00, R&D systems, Minneapolis, Minn.). Optical correction was performed as suggested by the manufacturer with absorbance at 540 nm. Absorbances were measured with a DTX 880 plate reader (Beckman Coulter).

Pharmacokinetic Analysis of TIC10

The absorbance profile of TIC10 was determined on a Gene Spec III spectrometer (Hitachi Solutions American, South San Francisco, Calif.). HPLC analysis was performed by absorbance detection at 239 nm on an Agilent 1200 series system (Agilent, Santa Clara, Calif.) using an Eclipse XDB-C18 column (Agilent) and a 100 µL injection loop. Isocratic elution at 1 mL/minute was carried out in 0.1% trifluoroacetic acid in $dH_2O$. An acetonitrile (ACN) gradient was carried out for elution as 15-20% ACN at 0-5 minutes, 20-23% for 5-12 minutes, 25% for 12-18 minutes. The standard curve was generated by spiking concentrations of TIC10 into plasma harvested from athymic nude mice from unrelated experiments. For all plasma samples, blood was obtained by terminal cardiac puncture of the left ventricle and collected into EDTA tubes (BD). Samples were centrifuged at 500 g for 10 minutes. Plasma was deproteinated by the adding 30 µL of perchloric acid to 100 µL of samples, vortexed for 15 seconds, centrifuged for 2 minutes, and the supernatant was immediately injected into the HPLC. AUC was normalized to an internal serum peak with a retention time of 8.1 minutes. AUC data versus time was fit with a two-compartment open model with first order elimination from central compartment using the equation $AUC=Ae^{-\alpha t}+Be^{-\beta t}$ where t=time and A and B are the extrapolated concentrations at the initiation of the two phases (distribution and elimination). Half-lives calculated as $t_{1/2\alpha}=0.693/\alpha$ and $t_{1/2\beta}=0.693/\beta$. Other equations used for calculation include $CL=dose/AUC_{0-\infty}$ and $V_d=dose/(AUC_{0-\infty}X\beta)$.

Gene Expression Analysis

HCT116 $p53^{-/-}$ cells were grown in log-phase and treated with DMSO or TIC10 (10 µM). At 48 hr, RNA was isolated using the RNeasy Mini Kit (Qiagen). Microarray analysis was performed using the Illumina HT-12 Beadchip (Illumina). RNA quality and concentration was assessed using an Agilent 2100 Bioanalyzer with RNA Nano LabChip® (Agilent). cRNA was synthesized by TotalPrep™ Amplification (Ambion) from 500 ng of RNA according to manufacturer's instructions. T7 oligo (dT) primed reverse transcription was used to produce first strand cDNA. cDNA then underwent second strand synthesis and RNA degradation by DNA Polymerase and RNase H, followed by filtration clean up. In vitro transcription (IVT) was employed to generate multiple copies of biotinylated cRNA. The labeled cRNA was purified using filtration, quantified by NanoDrop, and volume-adjusted for a total of 750 ng/sample. Samples were fragmented, and denatured before hybridization for 18 hr at 58° C. Following hybridization, beadchips were washed and fluorescently labeled. Beadchips were scanned with a BeadArray Reader (Illumina). A project was created with the resultant scan data imported into GenomeStudio 1.0 (Illumina). Results were exported to GeneSpring Gx11 (Agilent Technologies). Measurements less than 0.01 were then set to 0.01, arrays normalized to the $50^{th}$ percentile, and individual genes normalized to the median of controls. For network analysis of transcriptional changes induced by TIC10, the dataset was analyzed using the Ingenuity Pathway Analysis software (Ingenuity Systems).

Western Blot Analysis

Western blot analysis was conducted as described in Wang, W. et al., PNAS 103, 11003-11008, 2006, using NuPAGE 4-12% Bis-Tris and and visualized using Supersignal West Femto (Thermo Scientific) and X-ray film. Nuclear and cytoplasmic extracts were prepared using a cytoplasmic lysis buffer (10 mM HEPES, 10 mM KCl, and 2 mM $MgCl_2$, 1 mM DTT) followed by a nuclear lysis buffer (20 mM HEPES, 420 mM NaCl, 1.5 mM $MgCl_2$, 250 µM EDTA, 25% glycerol). For all lysis buffers, fresh protease inhibitor (Roche) and 1 mM sodium orthovanadate was added immediately prior to use.

Chromatin Immunoprecipitation Assays

Chromatin immunoprecipitation (ChIP) assays were carried out as described for the TRAIL promoter in Nebbioso, A., et al., Nat Med, 11(1), 77-84, 2005 using a ChIP grade antibody for Foxo3a (Abcam) or an equivalent concentration of rabbit IgG (SouthernBiotech) as a nonspecific control.

TIC10 Causes p53-Independent Transcriptional Induction of the TRAIL Gene.

A cell-based bioluminescence reporter screen conducted in TRAIL-resistant Bax-null HCT116 human colon cancer cells using the TRAIL gene promoter yielded the small molecule TIC10 as a TRAIL-inducing compound.

TIC10 induced TRAIL promoter-dependent transcriptional activity of a luciferase reporter construct under regulatory control of the first 504 base pairs of the TRAIL promoter which excludes the p53 DNA-binding response element identified in Takimoto et al., 2000, Oncogene 19, 1735-1743. FIG. 1 is a graph showing activity of luciferase reporter in HCT116 $Bax^{-/-}$ cells under transcriptional control of the first 504 base pairs of the human TRAIL gene promoter upstream of the start of transcription (n=3). Error bars indicate s.d. of replicates. *P<0.05 between the indicated condition and controls.

Figure 2:
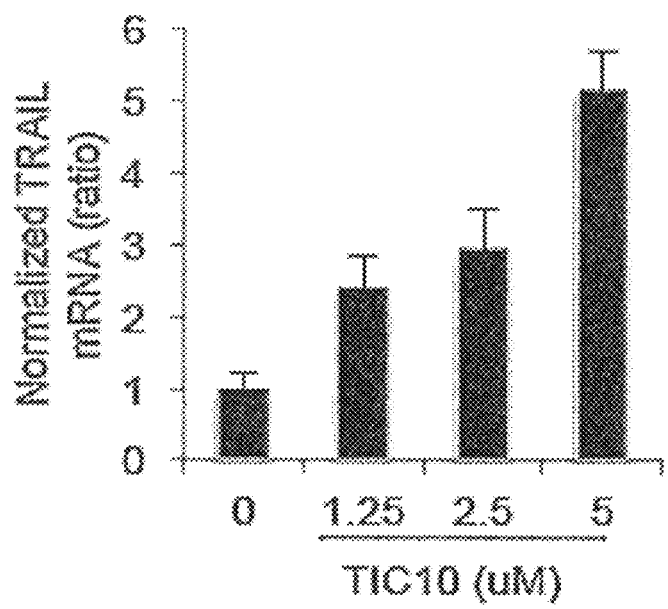
FIG. 2 is a graph showing RT-qPCR analysis of TRAIL mRNA levels in HCT116 p53$^{-/-}$ cells.
Figure 3:
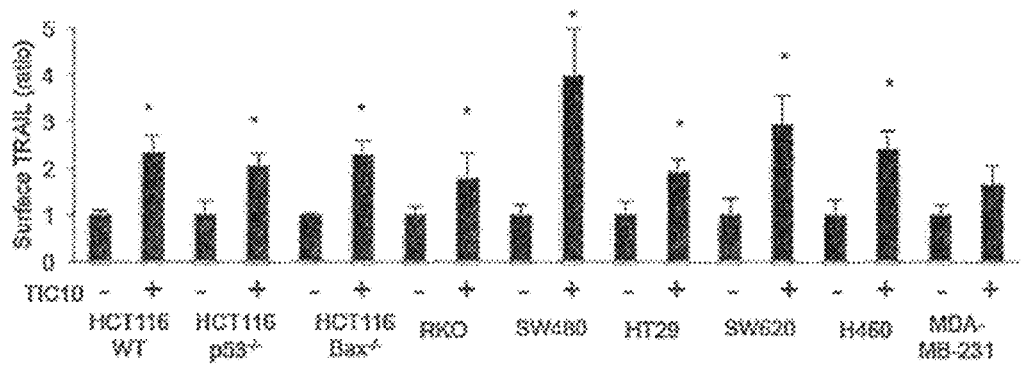
FIG. 3 is a graph showing surface TRAIL levels induced by TIC10 in a panel of cancer cells.

TIC10 caused a dose-dependent increase in TRAIL messenger-RNA. FIG. 2 is a graph showing RT-qPCR analysis of TRAIL mRNA levels in HCT116 $p53^{-/-}$ cells (48 hr, n=4). Error bars indicate s.d. of replicates.) TIC10 caused a dose-dependent increase in TRAIL protein localized to the cell surface of several cancer cell lines in a p53-independent manner. FIG. 3 is a graph showing surface TRAIL levels induced by TIC10 in a panel of cancer cells (10 µM, 72 hr, n=3). Error bars indicate s.d. of replicates. *P<0.05 between the indicated condition and controls.

Figure 4:
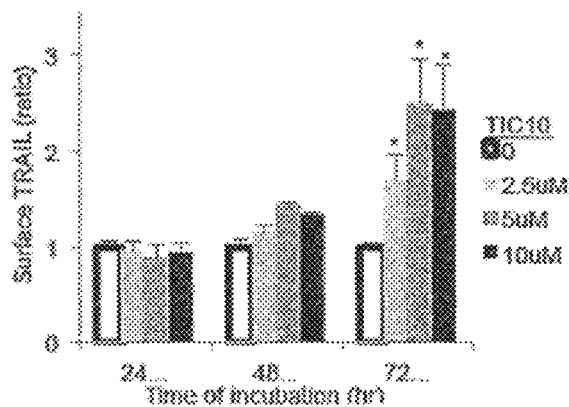
FIG. 4 is a graph showing surface TRAIL levels in HCT116 p53$^{-/-}$ cells following TIC10 treatment at indicated conditions and time points.
Figure 5:
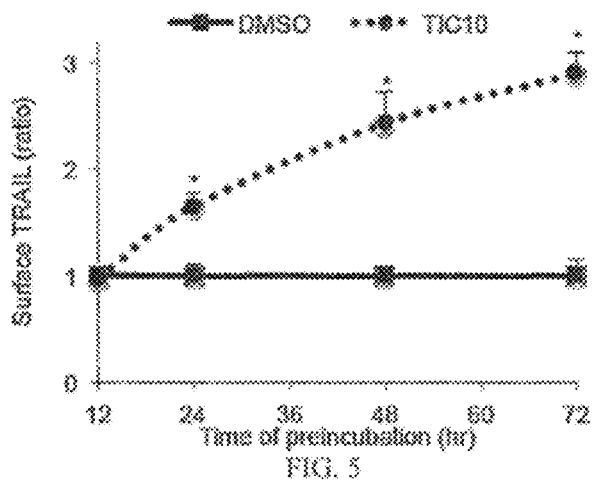
FIG. 5 is a graph showing HCT116 p53$^{-/-}$ TRAIL surface levels by flow cytometry at 72 hr following TIC10 treatment initiation.

TIC10 exposure leads to a significant and sustained presence of TRAIL on the cell surface of cancer cells. A time course analysis found that TRAIL was localized to the cell surface as a late event but that this induction could be temporally sustained even after removal of TIC10 from the media. FIG. 4 is a graph showing surface TRAIL levels in HCT116 $p53^{-/-}$ cells following TIC10 treatment at indicated conditions and time points (n=3). Error bars indicate s.d. of replicates. *P<0.05 between the indicated condition and controls. FIG. 5 is a graph showing HCT116 $p53^{-/-}$ TRAIL surface levels by flow cytometry at 72 hr following TIC10 treatment initiation (5 µM, n=3). Cells were treated for the indicated time of pre-incubation and then drug-free media was exchanged for the remaining time period until analysis at 72 hr. Error bars indicate s.d. of replicates. *P<0.05 between the indicated condition and controls.

TIC10 Induces TRAIL-Mediated Apoptosis

Figure 6:
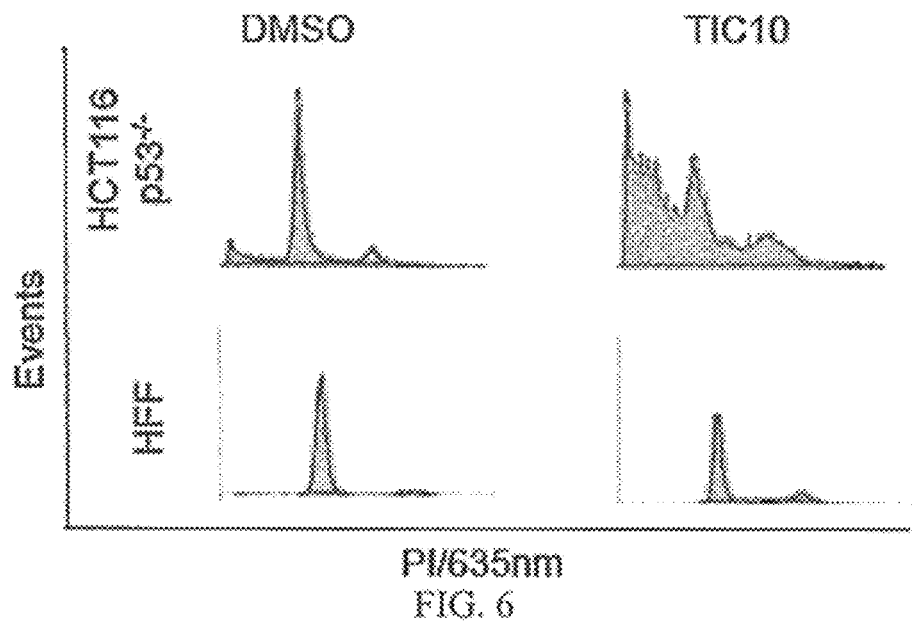
FIG. 6 shows cell cycle profiles of HCT116 p53$^{-/-}$ and human foreskin fibroblast (HFF) cells treated with TIC10.

TIC10 induced sub-G1 DNA content that was suggestive of cell death in TRAIL-sensitive HCT116 $p53^{-/-}$ cells without altering the cell cycle profiles of normal fibroblasts at equivalent doses. FIG. 6 shows cell cycle profiles of HCT116 $p53^{-/-}$ and HFF cells treated with TIC10 (5 µM, 72 hr, n=3).

Figure 7:
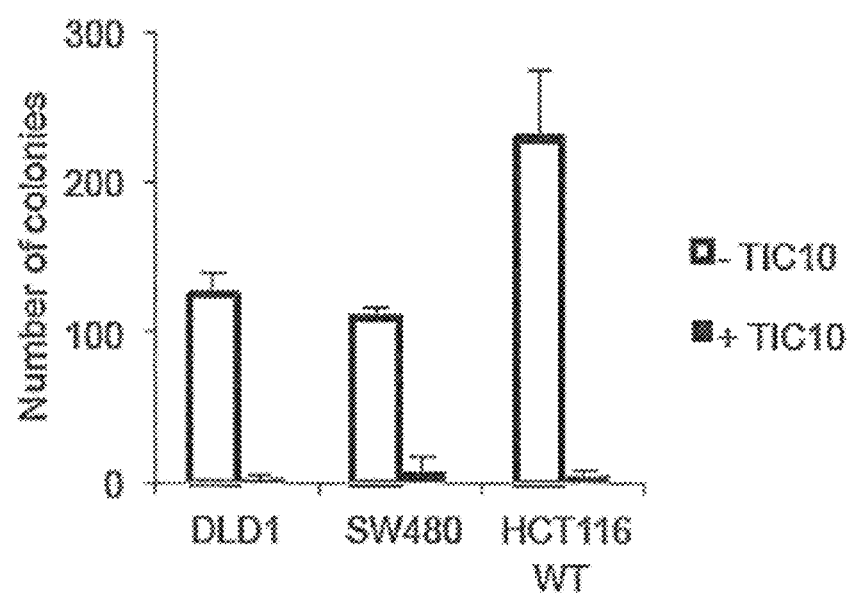
FIG. 7 is a graph showing quantification of colony formation assays of cancer cells treated with TIC10.
Figure 8:
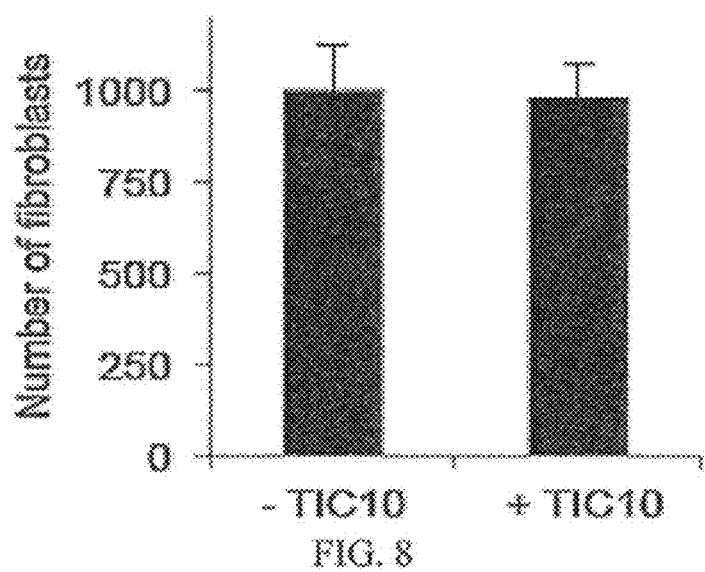
FIG. 8 is a graph showing parallel experiments as in FIG. 7 but with HFF cells that were enumerated at endpoint.

TIC10 decreased the clonogenic survival of cancer cell lines while sparing normal fibroblasts. FIG. 7 is a graph showing quantification of colony formation assays of cancer cells treated with TIC10 (10 µM, 72 hr, n=3). Error bars indicate standard deviation (s.d.) of replicates. FIG. 8 is a graph showing parallel experiments as in FIG. 7 but with HFF cells that were enumerated at endpoint (n=3). Error bars indicate standard deviation (s.d.) of replicates.

Figure 9:
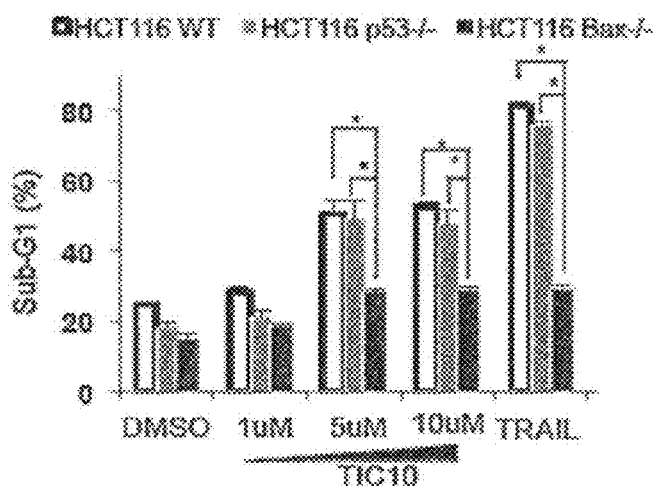
FIG. 9 is a graph showing sub-G1 analysis of HCT116 WT, p53$^{-/-}$, and Bax$^{-/-}$ cells following treatment with DMSO, TIC10 or rhTRAIL (25 ng/mL)

TIC10 induced sub-G1 content in a p53-independent and Bax-dependent manner. FIG. 9 is a graph showing sub-G1 analysis of HCT116 WT, $p53^{-/-}$, and $Bax^{-/-}$ cells following treatment with DMSO, TIC10 (1, 5, or 10 µM), or rhTRAIL (25 ng/mL) for 72 hr (n=3). Error bars indicate standard deviation (s.d.) of replicates. *P<0.05 between the indicated condition and control unless otherwise indicated.

Figure 10:
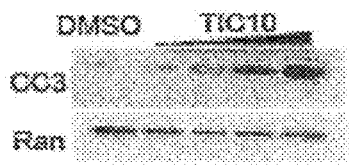
FIG. 10 is an image showing Western blot analysis results.
Figure 11:
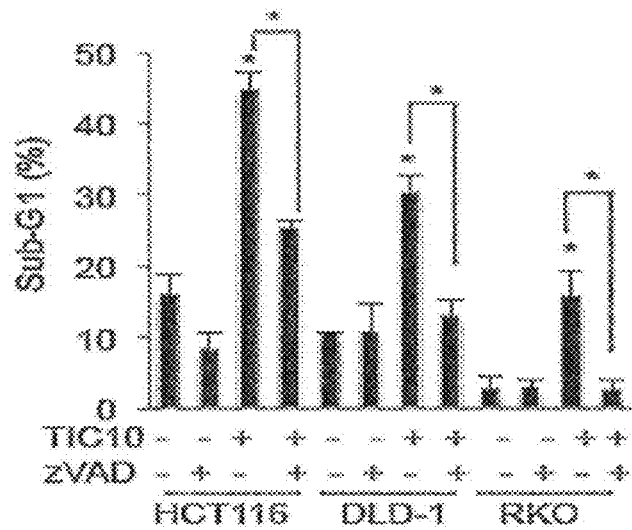
FIG. 11 is a graph showing sub-G1 analysis of TIC10-treated cancer cells pre-incubated with or without zVAD-fmk.

In accordance with apoptotic cell death, TIC10 increased active caspase-3 levels as indicated by immunofluorescence assay in HCT116 p53$^{-/-}$ cells treated with 5 µM TIC10 for 72 hr and by Western blot analysis in HCT116 p53$^{-/-}$ cells treated with 1 µM, 2.5 µM, 5 µM or 10 µM TIC10 for 72 hr. FIG. 10 is an image showing Western blot analysis results. TIC10 induced sub-G1 content was significantly inhibited by co-incubation with the pan-caspase apoptosis inhibitor zVAD-fmk. FIG. 11 is a graph showing sub-G1 analysis of TIC10-treated cancer cells pre-incubated with or without zVAD-fmk (10 µM, 72 hr, n=3). Error bars indicate standard deviation (s.d.) of replicates. *P<0.05 between the indicated condition and control unless otherwise indicated.

Figure 12:
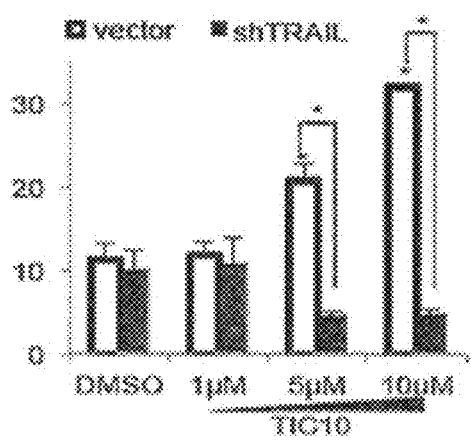
FIG. 12 is a graph showing sub-G1 analysis of MDA-MB-231 cells with stable knockdown of TRAIL by short hairpin RNA.
Figure 13:
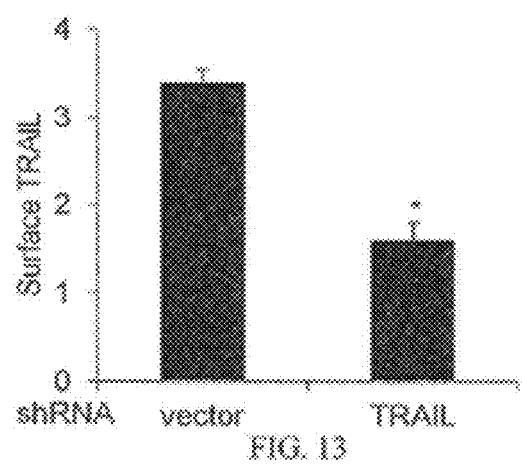
FIG. 13 is a graph showing verification of MDA-MB-231 shTRAIL knockdown by flow cytometry analysis of TIC10-treated cells.

TIC10-induced apoptosis appears to be specifically mediated by TRAIL, as indicated by inhibition of TIC10-induced cytotoxicity following stable knockdown of TRAIL by shRNA. FIG. 12 is a graph showing sub-G1 analysis of MDA-MB-231 cells with stable knockdown of TRAIL by short hairpin RNA (72 hr, n=3). Error bars indicate standard deviation (s.d.) of replicates. *P<0.05 between the indicated condition and control unless otherwise indicated. FIG. 13 is a graph showing verification of MDA-MB-231 shTRAIL knockdown by flow cytometry analysis of TIC10-treated cells (5 µM, 72 hr, n=3). Error bars indicate s.d. of replicates. *P<0.05 between the indicated condition and control unless otherwise indicated.

Figure 14:
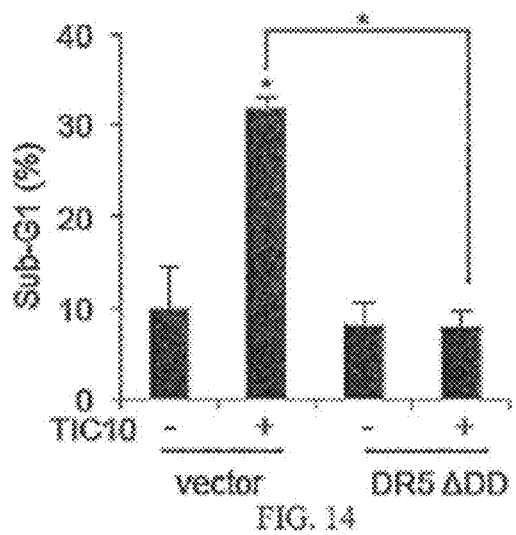
FIG. 14 is a graph showing sub-G1 analysis of TIC10-induced cell death in H460 cells with endogenous DR5 or overexpression of a DR5 construct with its death domain replaced by EGFP.

Additional evidence for the requirement of TRAIL in TIC10-induced tumor cell death was observed following disruption of the DR5 death-domain that modulates proapoptotic TRAIL signaling. FIG. 14 is a graph showing sub-G1 analysis of TIC10-induced cell death in H460 cells with endogenous DR5 or overexpression of a DR5 construct with its death domain replaced by EGFP (10 µM, 72 hr, n=3). Error bars indicate standard deviation (s.d.) of replicates. *P<0.05 between the indicated condition and control unless otherwise indicated.

Figure 15:
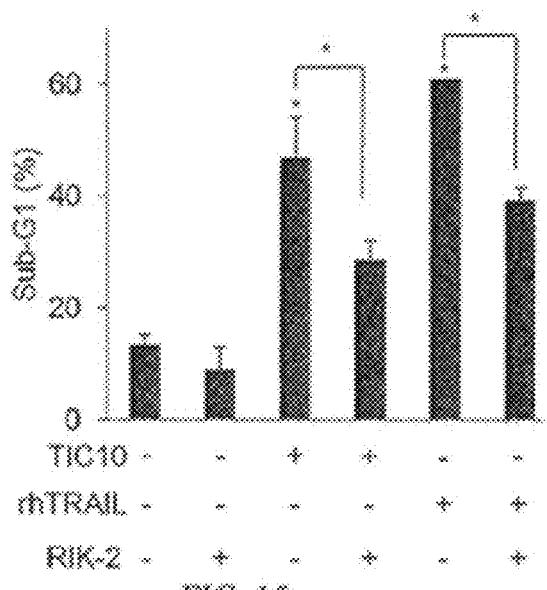
FIG. 15 is a graph showing sub-G1 analysis of HCT116 cells treated with DMSO, TIC10, or rhTRAIL in the presence or absence of a TRAIL-sequestering antibody, RIK-2.

Experimental sequestration of TRAIL by use of a blocking antibody showed the requirement of TRAIL in TIC10-induced tumor cell death. FIG. 15 is a graph showing sub-G1 analysis of HCT116 cells treated with DMSO, TIC10 (10 µM), or rhTRAIL (25 ng/mL) in the presence or absence of a TRAIL-sequestering antibody, RIK-2 (72 hr, n=3). Error bars indicate s.d. of replicates. *P<0.05 between the indicated condition and control unless otherwise indicated.

Figure 16:
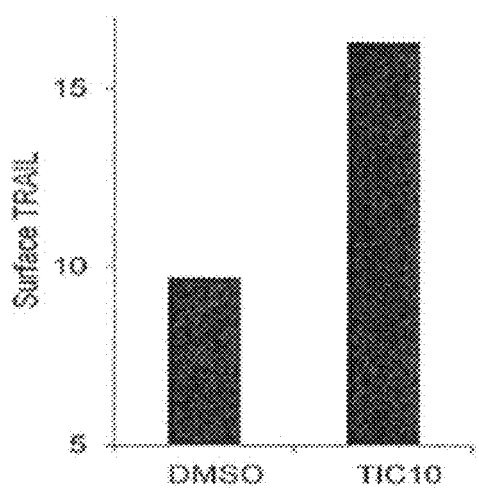
FIG. 16 is a graph showing TIC10-induced surface TRAIL with freshly resected human colon cancer cells.
Figure 17:
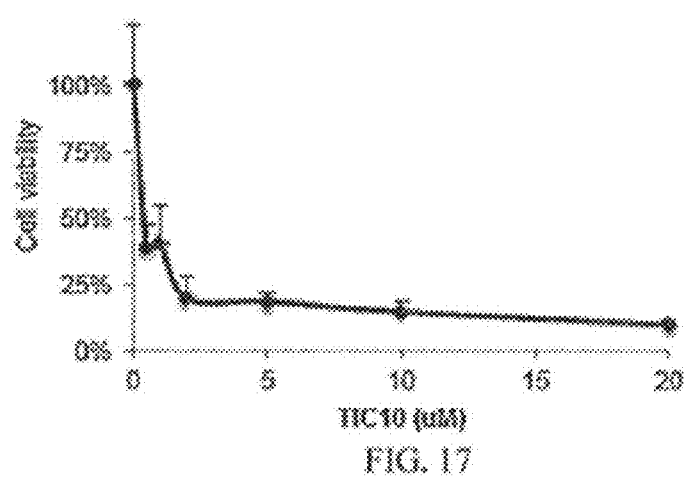
FIG. 17 is a graph showing results of a cell viability assay of primary colon cancer cells from FIG. 16 treated with DMSO, TIC10 or 5-FU.

The activity of TIC10 on freshly resected colon tumor cells from a human patient was examined and it was found that TIC10 induced TRAIL and potent cytotoxic effects unlike 5-FU. FIG. 16 is a graph showing TIC10-induced surface TRAIL with freshly resected colon cancer cells (10 µM, 72 hr). Tissue was a mucinous adenocarcinoma resected from an 85 year-old female patient. Data is expressed as median fluorescence intensity. FIG. 17 is a graph showing results of a cell viability assay of primary colon cancer cells from FIG. 16 treated with DMSO, TIC10 (0.6, 1.25, 2.5, 5, 10, 20 µM), or 5-FU (5 µM) (n=3). Error bars indicate s.d. of replicates.

Figure 18:
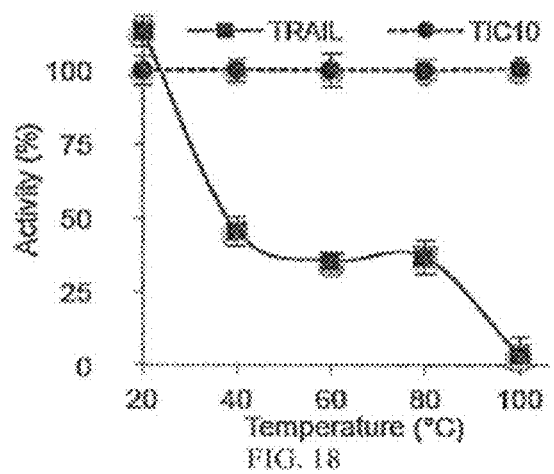
FIG. 18 is a graph showing ability of TIC10 or rhTRAIL to reduce cell viability in HCT116 cells following a 1 hr pre-incubation at the indicated temperatures.

The cytotoxic activity of TIC10 is thermally stable unlike TRAIL. FIG. 18 is a graph showing ability of TIC10 (5 µM) or rhTRAIL (25 ng/mL) to reduce cell viability in HCT116 cells following a 1 hr pre-incubation at the indicated temperatures (72 hr, n=3). Error bars indicate standard deviation (s.d.) of replicates.

TIC10 is a Potent TRAIL-Mediated Antitumor Agent In Vivo

Figure 19:
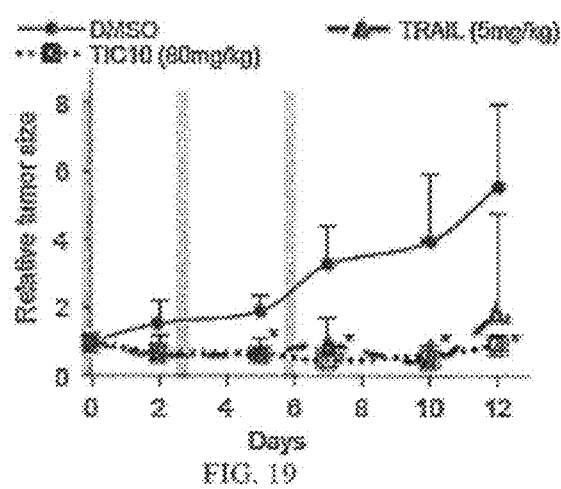
FIG. 19 is a graph showing HCT116 p53$^{-/-}$ xenograft treated with TIC10, TRAIL, or vehicle.

TIC10 caused tumor regression in the HCT116 p53$^{-/-}$ xenograft to a comparable extent to that observed with TRAIL when both were administered as multiple doses. FIG. 19 is a graph showing HCT116 p53$^{-/-}$ xenograft treated with 3 doses of TIC10 (i.p.), TRAIL (i.v.), or vehicle (i.p.) administered on day 0, 3, and 6 as indicated by gray vertical bars (n=10). Error bars indicate standard deviation (s.d.) of replicates. *P<0.05 and **P<0.005 between the indicated condition and control unless otherwise indicated.

Figure 20:
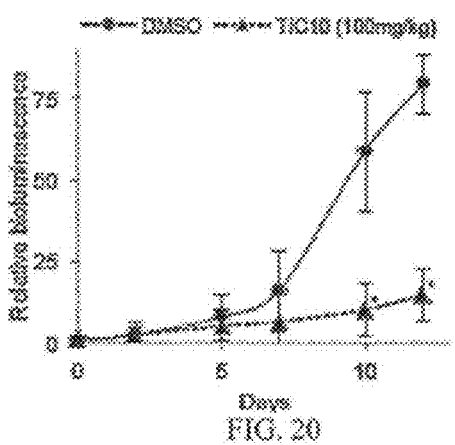
FIG. 20 is a graph showing results of bioluminescent imaging of luciferase-infected HCT116 p53$^{-/-}$ xenografts treated with TIC10 or vehicle.
Figure 21:
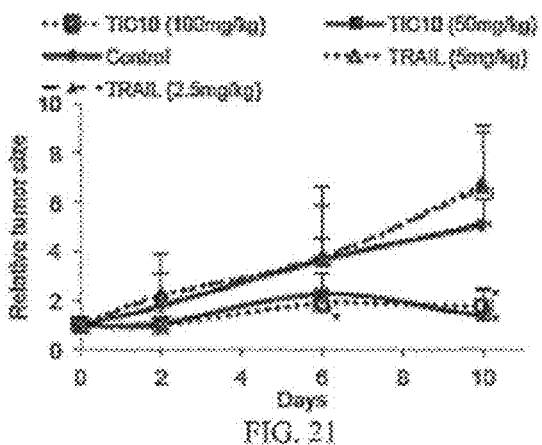
FIG. 21 is a graph showing RKO xenograft treated with TIC10, TRAIL or vehicle.

Single dose experiments in HCT116 WT) and RKO human colon cancer xenograft-bearing mice corroborated the potent anti-tumor activity of TIC10, and clearly demonstrated superiority TRAIL in the RKO xenograft under the given conditions. FIG. 20 is a graph showing results of bioluminescent imaging of luciferase-infected HCT116 p53$^{-/-}$ xenografts that received a single i.p. injection of TIC10 or vehicle (n=6). Error bars indicate standard deviation (s.d.) of replicates. *P<0.05 and **P<0.005 between the indicated condition and control unless otherwise indicated. FIG. 21 is a graph showing RKO xenograft with a single dose of TIC10 (i.p.), TRAIL (i.v.), or vehicle (i.p., n=10). Error bars indicate standard deviation (s.d.) of replicates. *P<0.05 and **P<0.005 between the indicated condition and control unless otherwise indicated.

Figure 22:
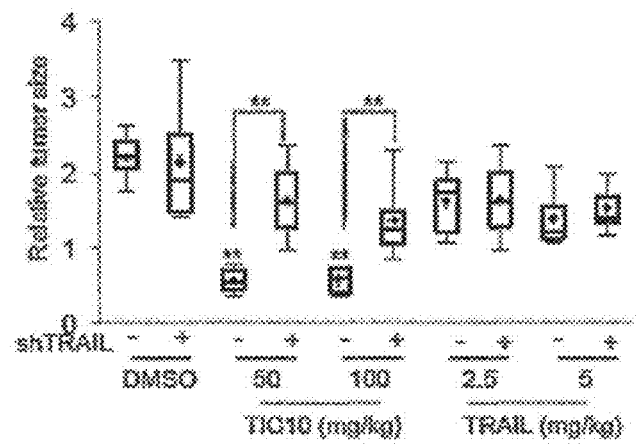
FIG. 22 is a box and whisker plot of tumor volume on day 9 following treatment initiation in MDA-MB-231 vector or shTRAIL xenografts with TIC10, TRAIL or vehicle.

TIC10 induced regression of MDA-MB-231 human breast cancer xenografts, an effect that was significantly inhibited by stable knockdown of TRAIL whereas TRAIL-treated tumors progressed. FIG. 22 is a box and whisker plot of tumor volume on day 9 following treatment initiation in MDA-MB-231 vector or shTRAIL xenografts with single doses of TIC10 (i.p.), TRAIL (i.v.), or vehicle (DMSO, i.p.) (n=8). Error bars indicate standard deviation (s.d.) of replicates. *P<0.05 and **P<0.005 between the indicated condition and control unless otherwise indicated. TUNEL staining of tumors from the MDA-MB-231 vector and shTRAIL xenografts 2 days post-treatment with 50 mg/kg or 100 mg/kg TIC10 show increased TUNEL staining in vector-treated no shTRAIL-treated cells.

Figure 23:
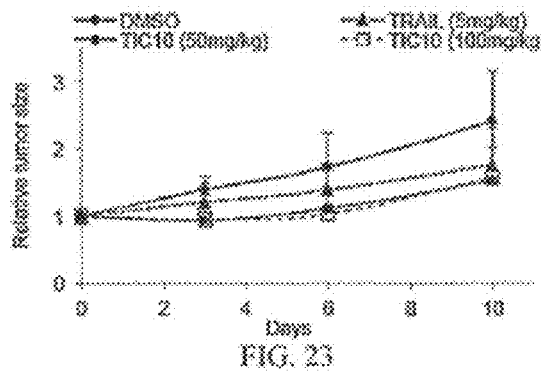
FIG. 23 is a graph showing relative tumor volume of DLD-1 xenografts treated with TRAIL, TIC10 or DMSO.

This directly demonstrates that the anti-tumor activity of TIC10 is superior to that of TRAIL when administered as single doses under these conditions and is modulated at least in part by TRAIL produced by tumor cells. In DLD-1 xenografts, TIC10 induced tumor stasis at 1 week post-treatment while TRAIL-treated tumors progressed after a single dose. FIG. 23 is a graph showing relative tumor volume of DLD-1 xenografts treated with TRAIL (i.v.), TIC10 (i.p.), or DMSO (i.p.) as a single dose at day 0 at indicated concentrations (n=8).

Figure 24:
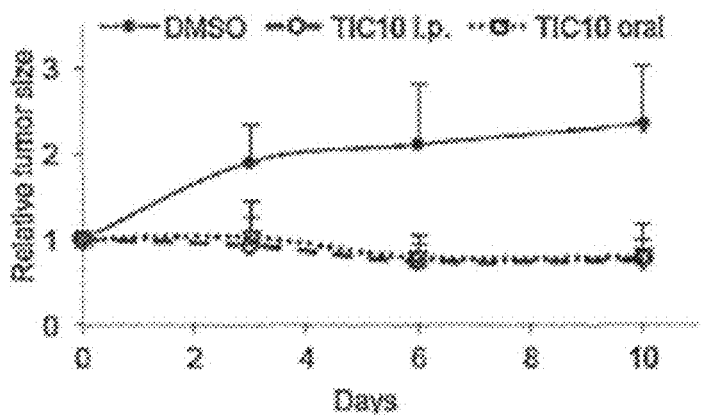
FIG. 24 is a graph showing comparison of i.p. versus oral administration of TIC10 in SW480 xenografts.

TIC10 also induced a sustained regression of the SW480 xenograft as a single dose by intraperitoneal or oral delivery, suggesting favorable bioavailability. FIG. 24 is a graph showing comparison of i.p. versus oral administration of a single dose of TIC10 at 30 mg/kg in SW480 xenografts treated on day 0 (n=6).

Figure 25:
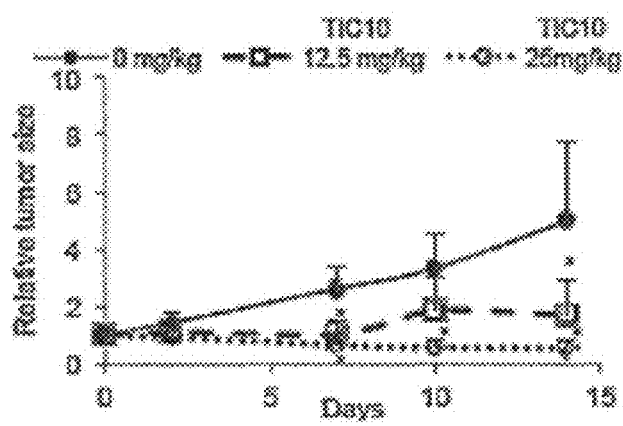
FIG. 25 is a graph showing TIC10 or vehicle administered as a single oral dose in the HCT116 xenograft.

Titration of a single dose of orally administered TIC10 in the HCT116 xenograft model revealed sustained anti-tumor efficacy at 25 mg/kg. FIG. 25 is a graph showing TIC10 or vehicle administered as a single oral dose in the HCT116 xenograft (n=6). Error bars indicate standard deviation (s.d.) of replicates. *P<0.05 and **P<0.005 between the indicated condition and control unless otherwise indicated.

Figure 26:
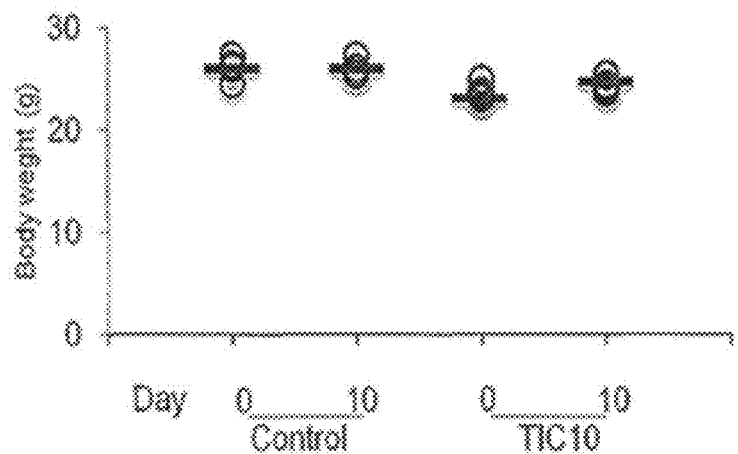
FIG. 26 is a graph showing body weight of athymic, female nude mice treated with a single dose of TIC10.
Figure 27:
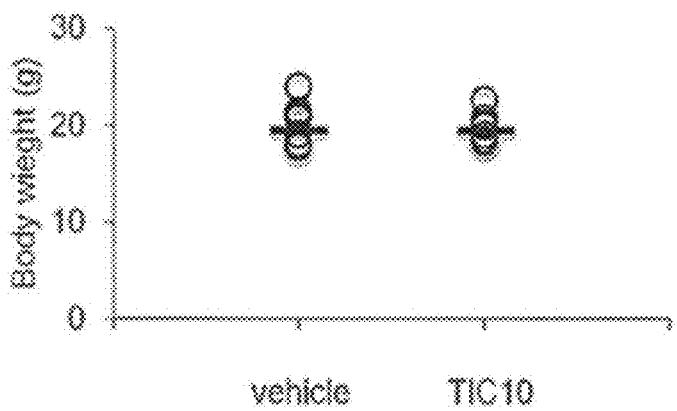
FIG. 27 is a graph showing body weight of C57/B6 female mice at the end of week 4 of treatment with oral TIC10.

The lack of apparent toxicity at multiple doses delivered at 4-fold above this therapeutic dose in a previous xenograft along with no adverse effects on body weight or liver histology suggests that TIC10 has a wide therapeutic window. FIG. 26 is a graph showing body weight of athymic, female nude mice treated with a single dose of TIC10 (100 mg/kg, i.p.). FIG. 27 is a graph showing body weight of C57/B6 female mice at the end of week 4 of treatment with a single weekly dose of oral TIC10 (25 mg/kg) for 4 weeks. Histologic analysis by H&E staining of liver from athymic, female nude mice harvested 3 days post-treatment with TIC10 (100 mg/kg, i.p.) showed no apparent toxicity of TIC10.

Chronic exposure to oral TIC10 at 25 mg/kg weekly for 4 weeks in immuno-competent mice did not cause any changes in a panel of serum chemistry markers as shown in Tables IA and IB.

Tables IA and IB show serum chemistry of C57/B6 mice treated with vehicle or TIC10 (25 mg/kg) weekly for 4 weeks.

TABLE IA

| Cohort | Sodium (mM) | Potassium (mM) | Chloride (mM) | Total bilirubin (mg/dl) | Blood urea nitrogen (mg/dl) |
|---|---|---|---|---|---|
| Control | 151.5 ± 4.2 | 9.025 ± 2.2 | 106.75 ± 1.7 | 3.075 ± 1.6 | 26 ± 1.6 |
| TIC10 | 154.5 ± 5.2 | 7.325 ± 3.2 | 104 | 2.725 ± 2.4 | 33.75 ± 7.3 |

TABLE IB

| Cohort | Creatinine (mg/dl) | Total Protein (g/dl) | Albumin (g/dl) | Alkaline phosphate (U/L) | Lactate dehydrogenase (U/L) |
|---|---|---|---|---|---|
| Control | 0.25 ± .06 | 4.9 ± .36 | 3 ± .08 | 104.5 | 265 |
| TIC10 | 0.15 ± .06 | 4.97 ± .61 | 2.9 | 112 ± 12 | 287.5 ± 125 |

Figure 28:
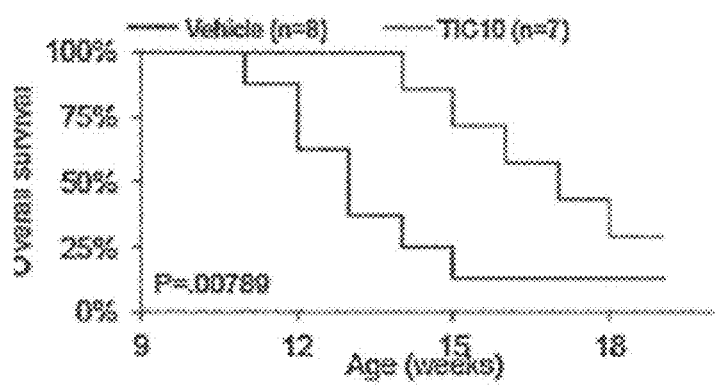
FIG. 28 is a graph showing overall survival of Eμ-myc treated during weeks 9-12 with weekly oral TIC10.

To test the efficacy of TIC10 in an immuno-competent preclinical cancer model, Eµ-Myc transgenic mice that spontaneously develop lymphoma were used. The same oral dosing schedule as above that was demonstrated to be safe from weeks 9-12 of age was used. TIC10 significantly prolonged the survival of these mice by 4 weeks. FIG. 28 is a graph showing overall survival of Eµ-myc treated during weeks 9-12 with weekly oral TIC10 (25 mg/kg). P value determined by log-rank test. For relative tumor volume plots, tumor size is expressed relative to the tumor size on day 0, which is defined as the day of treatment initiation. Histologic analysis by H&E staining of Eµ-myc and WT C57/B6 axillary lymph nodes at 14 weeks of age showed no apparent toxicity of TIC10.

Synergistic Combinations of TIC10 and Chemotherapeutic Agents

Figure 29:
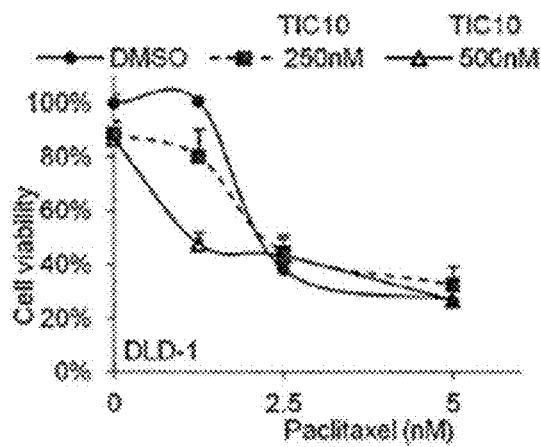
FIG. 29 is a graph showing cell viability of DLD-1 cells treated with TIC10 in combination with paclitaxel.
Figure 30:
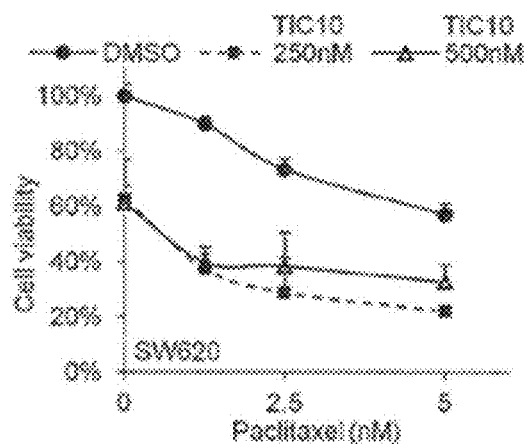
FIG. 30 is a graph showing cell viability of SW620 cells treated with TIC10 in combination with paclitaxel.
Figure 31:
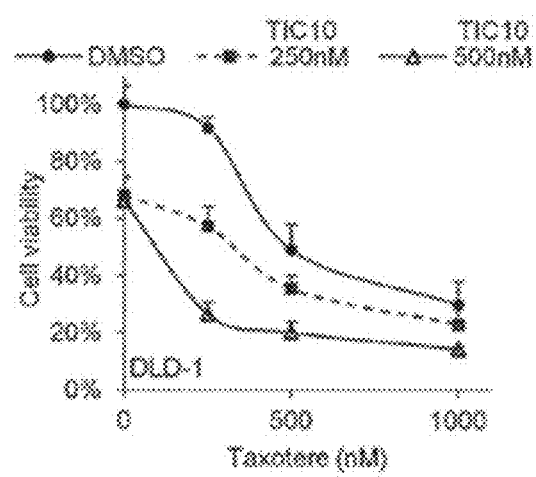
FIG. 31 is a graph showing cell viability of DLD-1 cells treated with TIC10 in combination with taxotere.
Figure 32:
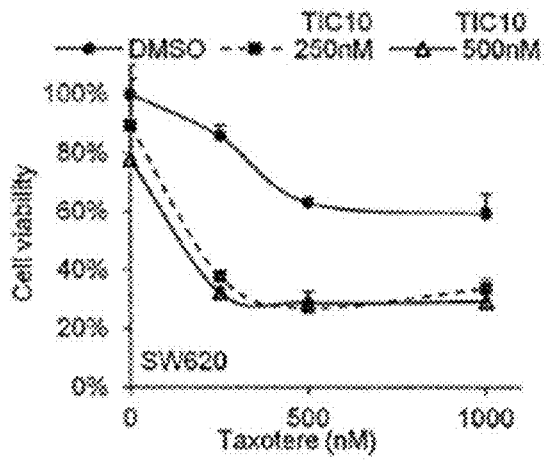
FIG. 32 is a graph showing cell viability of SW620 cells treated with TIC10 in combination with taxotere.

Syrprisingly, in vitro synergy between TIC10 and the taxanes paclitaxel and docetaxel (trade name Taxotere) is observed. FIG. 29 is a graph showing cell viability of DLD-1 treated with TIC10 in combination with paclitaxel in at indicated conditions (72 hr, n=3). Error bars indicate s.d. of replicates. FIG. 30 is a graph showing cell viability of SW620 cells treated with TIC10 in combination with paclitaxel in at indicated conditions (72 hr, n=3). Error bars indicate s.d. of replicates. FIG. 31 is a graph showing cell viability of DLD-1 cells treated with TIC10 in combination with taxotere in at indicated conditions (72 hr, n=3). Error bars indicate s.d. of replicates. FIG. 32 is a graph showing cell viability of SW620 cells treated with TIC10 in combination with taxotere in at indicated conditions (72 hr, n=3). Error bars indicate s.d. of replicates.

Figure 33:
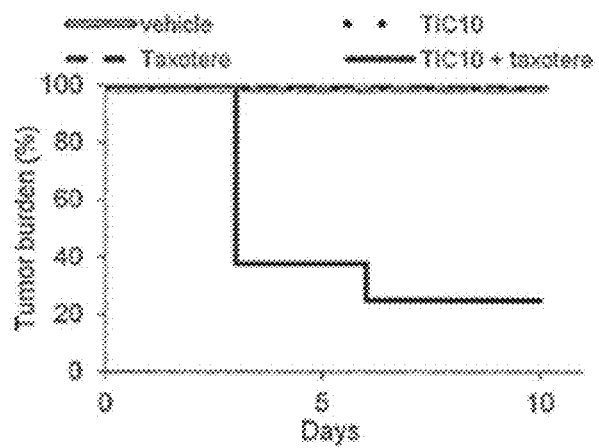
FIG. 33 is a graph showing percent of cohorts in H460 xenograft that retain tumor burden following treatment with TIC10 or taxotere alone, in combination, or with vehicle.
Figure 34:
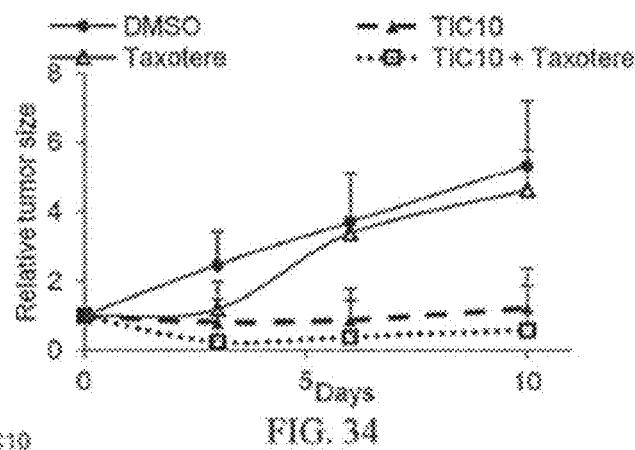
FIG. 34 is a graph showing a relative tumor volume plot for FIG. 33.

The combination of TIC10 and either taxane paclitaxel or docetaxel cooperated to yield sustained cures in the H460 non-small cell lung cancer xenograft. FIG. 33 is a graph showing percent of cohorts in H460 xenograft that retain tumor burden following treatment with TIC10 (30 mg/kg, i.p.) or taxotere (20 mg/kg, i.v.) alone, in combination, or with vehicle (DMSO, i.p.) (n=8) as single doses. FIG. 34 is a graph showing a relative tumor volume plot for FIG. 33. Error bars indicate s.d. of replicates.

Figure 35:
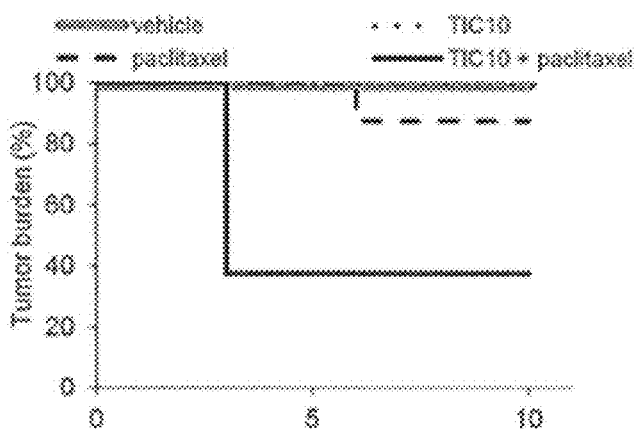
FIG. 35 is a graph showing percent of cohorts in H460 xenograft that retain tumor burden following treatment with TIC10 or paclitaxel alone, in combination, or with vehicle.
Figure 36:
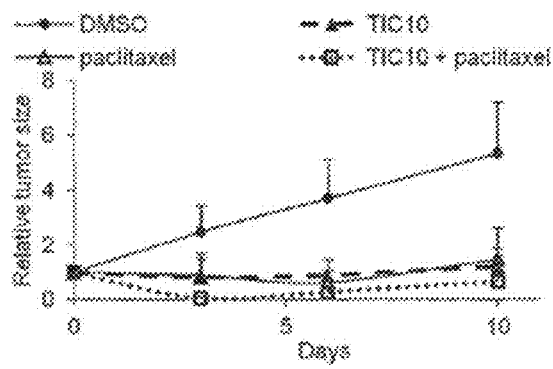
FIG. 36 is a graph showing a relative tumor volume plot for FIG. 35.

FIG. 35 is a graph showing percent of cohorts in H460 xenograft that retain tumor burden following treatment with TIC10 (30 mg/kg, i.p.) or paclitaxel (20 mg/kg, i.v.) alone, in combination, or with vehicle (DMSO, i.p.) (n=8) as single doses. FIG. 36 is a graph showing a relative tumor volume plot for FIG. 35. Error bars indicate s.d. of replicates.

Figure 37:
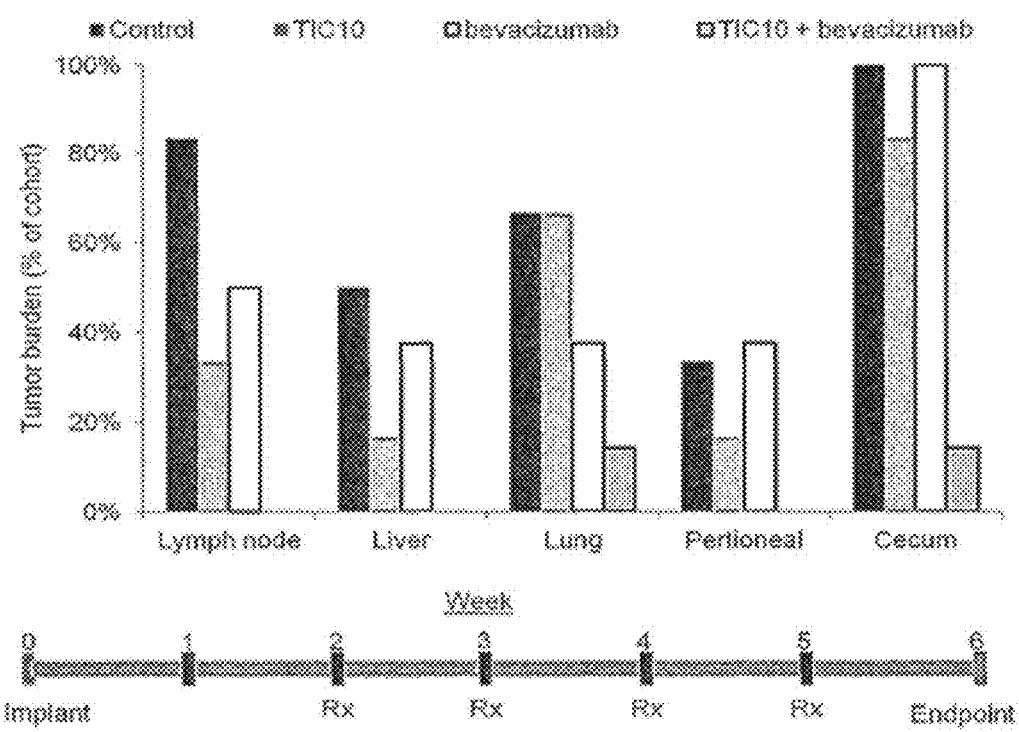
FIG. 37 is a graph showing percent of cohorts with implanted with intracecal HCT116 p53$^{-/-}$ tumors with evident tumors at the primary and distal sites at endpoint, treated with TIC10, bevacizumab or a combination of TIC10 and bevacizumab.

TIC10 was found in this example to cooperate with bevacizumab when both were given once a week in a metastatic orthotopic mouse model of p53-deficient colorectal cancer to reduce tumor incidence at the primary cecal tumor and distal metastatic sites including the lung, liver, lymph nodes and peritoneum. FIG. 37 is a graph showing percent of cohorts with implanted with intracecal HCT116 p53$^{-/-}$ tumors with evident tumors at the primary and distal sites at endpoint (n=5). As indicated by time line, treatment was administered once a week starting at 2 weeks post-implantation with cohorts receiving vehicle, TIC10 (25 mg/kg, oral), bevacizumab (bev, 10 mg/kg, i.v.), or the combination of TIC10 and bevacizumab.

Figure 38:
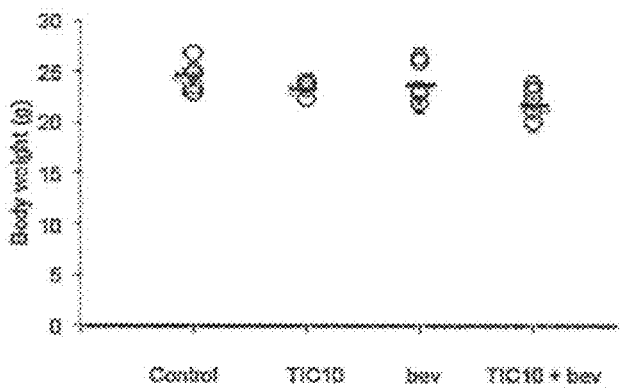
FIG. 38 is a graph showing body weight of mice implanted with intracecal HCT116 p53$^{-/-}$ tumors treated with vehicle, TIC10, bevacizumab or a combination of TIC10 and bevacizumab.

TIC10 alone and in combination with bevacizumab was well tolerated and caused no significant changes in body weight at endpoint with this multi-dose regimen. FIG. 38 is a graph showing body weight of mice at endpoint. Error bars indicate s.d. of replicates.

TIC10 Causes Tumor-Specific Cell Death by TRAIL-Mediated Direct and Bystander Effects Immunohistochemical (IHC) analysis of HCT116 p53$^{-/-}$ xenograft tumors following a single dose of TIC10 on day 0 (100 mg/kg, i.p.). revealed increased protein levels of TRAIL and cleaved caspase-8, the initiator caspase involved in TRAIL-mediated apoptosis.

Fragmented nuclei observed by histology and increased TUNEL (TdT-mediated dUTP Nick-End Labeling) staining further confirmed that TIC10 induced apoptosis in the treated tumors. Furthermore, TIC10 not only induced TRAIL in the tumor but also in stromal fibroblasts bordering the tumor as shown by H&E and IHC analysis for TRAIL at the border of tumor and stromal fibroblasts from HCT116 p53$^{-/-}$ xenograft tumors following treatment with TIC10 (100 mg/kg, i.p.) or vehicle on day 2 post-treatment.

Figure 39:
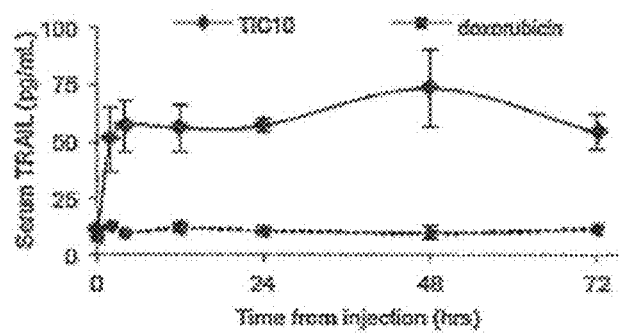
FIG. 39 is a graph showing TRAIL serum levels in tumor-free mice following TIC10 or doxorubicin.

Noting the TIC10-induced TRAIL expression in fibroblasts, soluble TRAIL In TIC10-treated non-tumor-bearing mice was assayed in to determine if normal cells secrete TRAIL in response to TIC10. TIC10 rapidly elevates serum levels of TRAIL in a manner that last for greater than 72 hours, longer than the serum half-life of recombinant TRAIL (~30 minutes). FIG. 39 is a graph showing TRAIL serum levels in tumor-free mice following TIC10 (100 mg/kg, i.v.) or doxorubicin (30 mg/kg, i.p.) (n=2). Error bars indicate s.d. of replicates.

Figure 40:
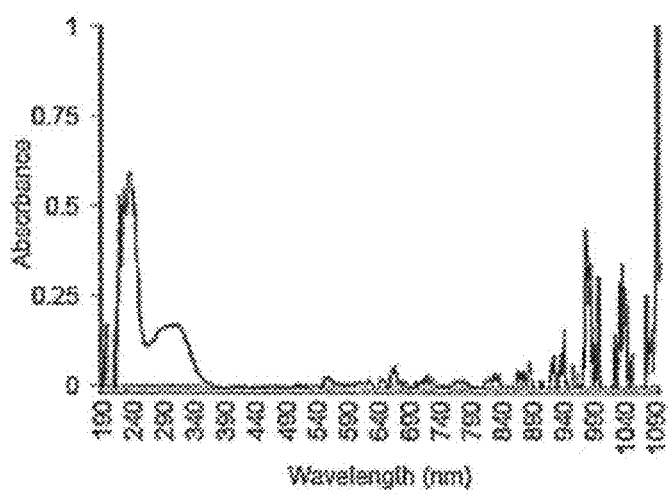
FIG. 40 is a graph showing the absorbance profile of TIC10 with a peak absorbance at 239 nm.
Figure 41:
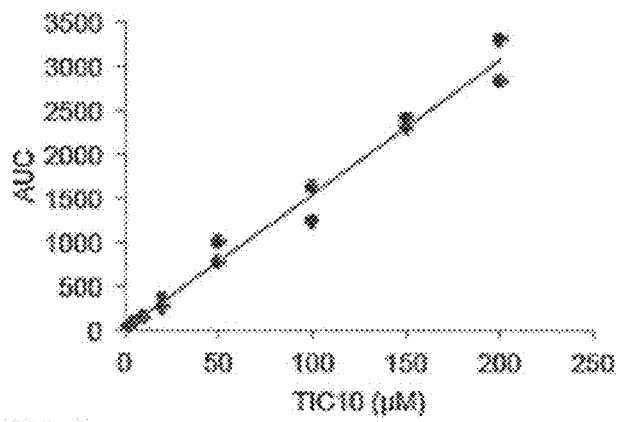
FIG. 41 is a graph showing a calibration curve for TIC10 spiked into mouse plasma and quantitated by HPLC analysis using area under curve (AUC)
Figure 42:
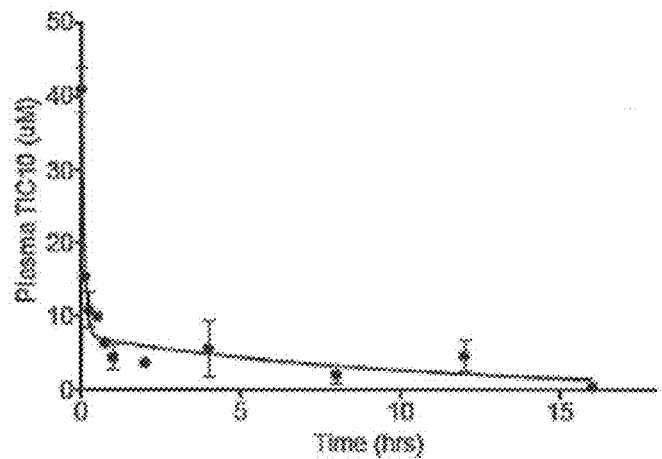
FIG. 42 is a graph showing plasma concentrations of TIC10 following intravenous administration in C57/B6 female mice.

Serum TRAIL induced by TIC10 was detected as soon as 2 hours following administration, which is more rapid that the kinetics observed in vitro in examples described herein. Pharmacokinetic analysis revealed that TIC10 is quickly distributed and has a plasma half-life of ~6.5 hours. Table II shows results of pharmacokinetic analysis of TIC10 in plasma of C57B6 mice. FIG. 40 is a graph showing the absorbance profile of TIC10 with a peak absorbance at 239 nm FIG. 41 is a graph showing a calibration curve for TIC10 spiked into mouse plasma and quantitated by HPLC analysis using area under curve (AUC). FIG. 42 is a graph showing plasma concentrations of TIC10 following intravenous administration at 25 mg/kg in C57/B6 female mice (n=3). Error bars represent standard error mean of replicates.

TABLE II

| Dose (mg/kg) | $t_{max}$ (h) | $C_{max}$ (μM) | A (h) | B (h) | α (1/h) | β (1/h) | $t_{1/2α}$ (h) | $t_{1/2β}$ (h) | $AUC_{0-\infty}$ (μM · h) | CL (L/h/kg) | Vd (L/kg) |
|---|---|---|---|---|---|---|---|---|---|---|---|
| 25 | 0.02 | 44.2 | 44.6 | 7.67 | 14.9 | 0.108 | 0.047 | 6.42 | 63.9 | 1.01 | 9.39 |

TIC10 has a longer half-life than recombinant TRAIL and that the effects of TIC10, i.e. TRAIL induction, are temporally sustained for days in vivo as seen in vitro.

IHC analysis of normal tissues in athymic, nude non-tumor bearing mice following TIC10 administration on day 0 (100 mg/kg, i.v.) revealed that TRAIL is upregulated at the protein level in the brain, kidney, and spleen of mice without apparent toxicity as determined by histology and TUNEL staining. TRAIL upregulation in response to TIC10 was not noted in other tissues including the liver at any time point.

The effects of TIC10 on normal fibroblasts and its selectivity for normal cells was tested in this example. TIC10 selectively induced apoptosis in p53-deficient tumor cells but not normal fibroblasts in co-culture experiments, using HCT116 p53$^{-/-}$ and HFF cells treated with TIC10 (10 μM) or DMSO for 3 days.

Figure 43:
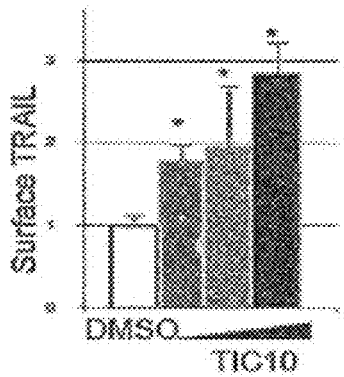
FIG. 43 is a graph showing surface TRAIL analysis of HFF cells following TIC10 treatment, 0, 2.5, 5, or 10 μM from left to right.

TIC10 induces a significant though modest amount of TRAIL on the surface of normal fibroblasts. FIG. 43 is a graph showing surface TRAIL analysis of HFF cells following TIC10 treatment (0, 2.5, 5, or 10 μM from left to right) (72 hr, n=3). Error bars indicate s.d. of replicates. *P<0.05 between the indicated condition and control unless otherwise indicated.

Figure 44:
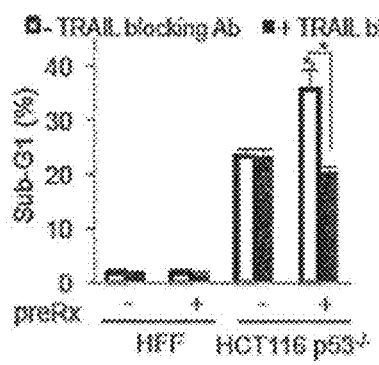
FIG. 44 is a graph showing sub-G1 analysis of a co-culture of HCT116 p53$^{-/-}$ cells and pretreated HFFs.

To test whether normal cells contribute to the anti-tumor efficacy of TIC10 through a TRAIL-mediated bystander effect normal fibroblasts preincubated with TIC10 were transplanted into co-culture with p53-deficient colon cancer cells. This resulted in a modest but significant increase in TRAIL-specific cell death of the cancer cell sub-population. FIG. 44 is a graph showing sub-G1 analysis of a co-culture of HCT116 p53$^{-/-}$ cells and pretreated HFFs (24 hr, n=3). HFF pretreatment consisted of 72 hr incubation with TIC10 (10 μM) or DMSO. These experiments were performed in the presence or absence of a TRAIL sequestering antibody (RIK-2). Scale bars are 100 μm. Error bars indicate s.d. of replicates. *P<0.05 between the indicated condition and control unless otherwise indicated.

Thus as demonstrated herein, TIC10 has a favorable therapeutic index and induces TRAIL in tumor, stromal, and normal cells that may contribute to the anti-tumor efficacy of TIC10 through both direct as well as bystander mechanisms.

TIC10 is an Effective Antitumor Agent in Glioblastoma Multiforme (GBM)

Figure 45:
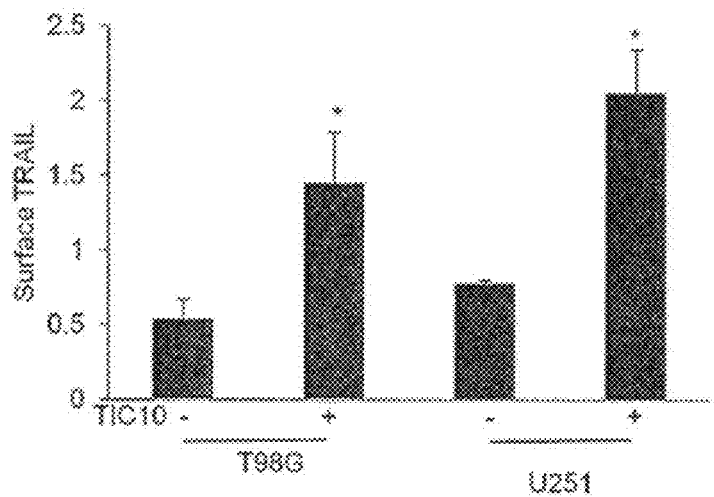
FIG. 45 is a graph showing surface TRAIL in GBM cell lines following incubation with TIC10.
Figure 46:
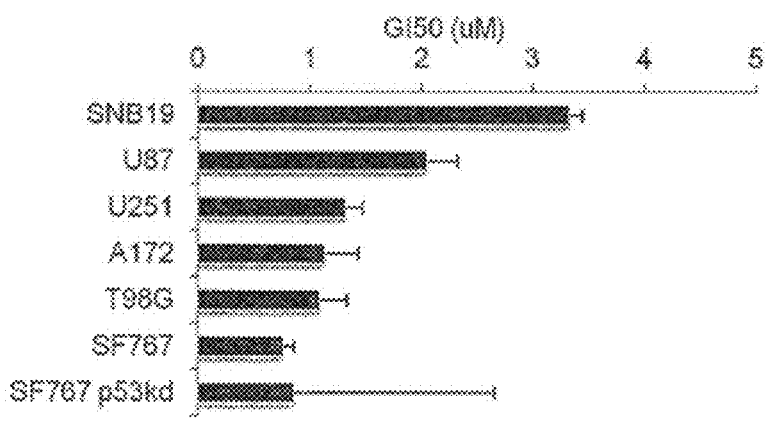
FIG. 46 is a graph showing GI50 values extrapolated from cell viability assays of indicated GBM cell lines at 72 hr post-treatment with TIC10 or DMSO.

TIC10 induces TRAIL in the brain and is useful as an anti-tumor agent against brain tumors. The activity of TIC10 in GBM cell lines was tested in this example and it was found that TIC10 induced TRAIL and had a p53-independent GI50 in the low micromolar range that is comparable with other cancer cell lines. FIG. 45 is a graph showing surface TRAIL in GBM cell lines following incubation with TIC10 (5 μM, 72 hr, n=3). *P<0.05 between the indicated condition and control. FIG. 46 is a graph showing GI50 values extrapolated from cell viability assays of indicated GBM cell lines at 72 hr post-treatment with TIC10 or DMSO (n=3).

Figure 47:
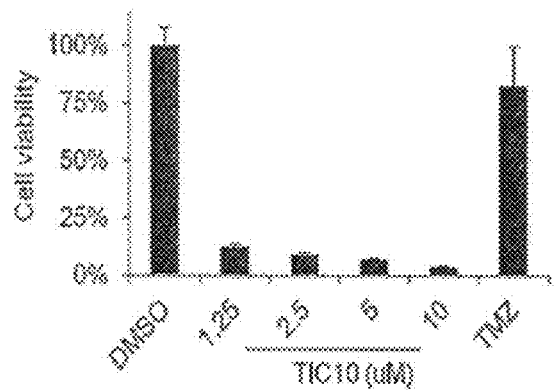
FIG. 47 shows results of a cell viability assay of freshly resected human glioblastoma tissue treated with DMSO, TIC10, or temozolomide.

TIC10 has cytotoxic effects on freshly isolated GBM cells that were temozolomide-resistant and previously irradiated in this example. FIG. 47 shows results of a cell viability assay of freshly resected glioblastoma tissue treated with DMSO, TIC10, or temozolomide (TMZ, 10 μM) (72 hr, n=3). Tissue was a grade IV glioblastoma with oligodendroglial component taken from a 38 year-old female patient who had undergone prior cytoreductive surgery and radiation.

Figure 48:
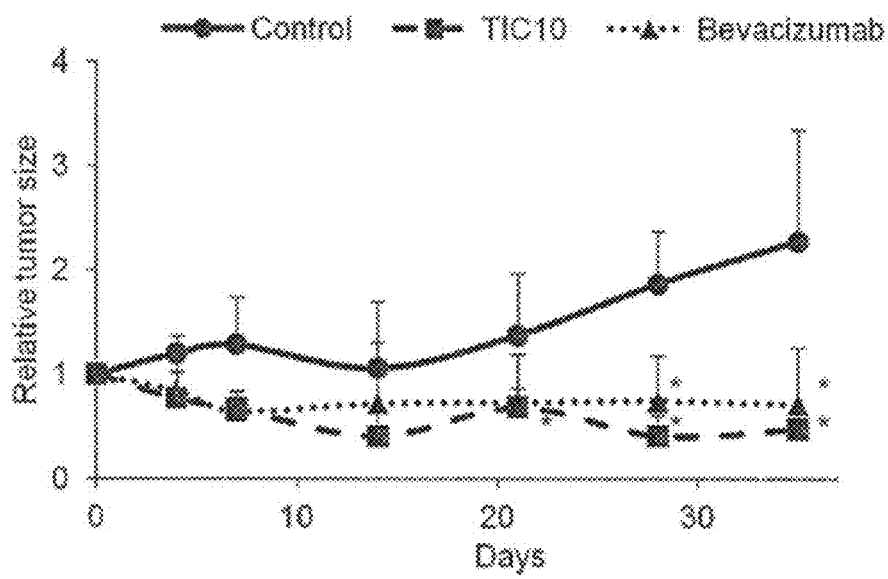
FIG. 48 is a graph showing subcutaneous xenograft of T98G with mice receiving a single dose of vehicle, TIC10 or bevacizumab.

TIC10 was tested in preclinical models of GBM as a monoagent and in combination with bevacizumab. TIC10 exerted p53-independent cytotoxicity against a panel of GBM cell lines, including temozolomide-resistant GBM cell lines such as T98G, and induced a sustained regression of subcutaneous T98G xenografts to an extent similar to bevacizumab when given as a single oral dose. FIG. 48 is a graph showing subcutaneous xenograft of T98G with mice receiving a single dose of vehicle, TIC10 (30 mg/kg, PO), or bevacizumab (10 mg/kg, i.v.) on day 0 (n=8). *P<0.05 between the indicated condition and control.

A single dose of TIC10 significantly doubled the overall survival of mice as a monoagent in an aggressive intracranial xenograft of human GBM using the SF767 cell line and cooperated with bevacizumab to triple the duration of survival of such brain tumor-bearing mice.

Figure 49:
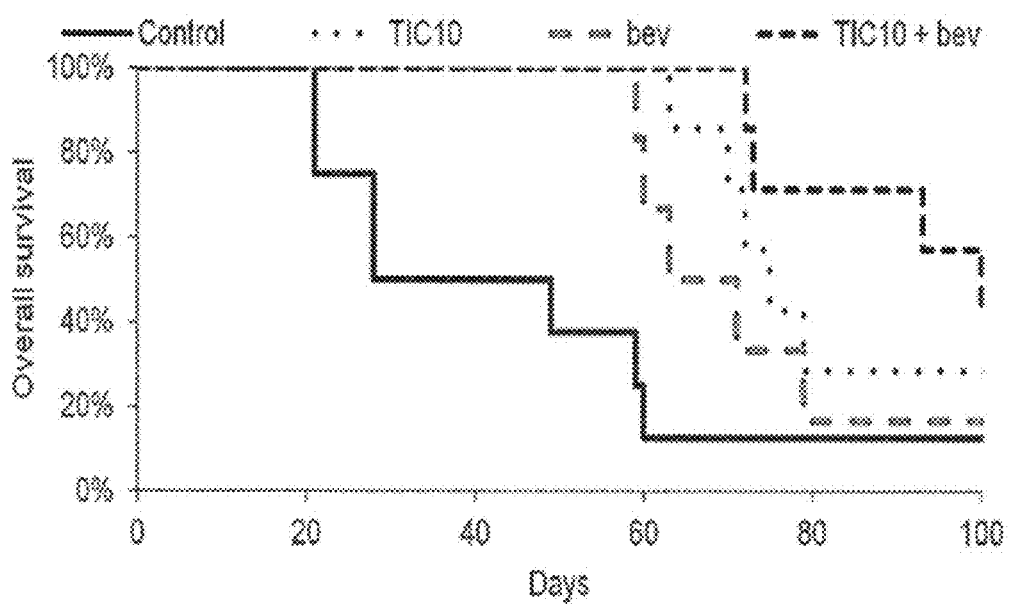
FIG. 49 is a graph showing overall survival of mice harboring SF767 intracranial tumors treated with a single oral dose of vehicle, TIC10, bevacizumab, or TIC10 and bevacizumab.

FIG. 49 is a graph showing overall survival of mice harboring SF767 intracranial tumors treated with a single oral dose of vehicle (n=8), TIC10 (25 mg/kg, n=7), bevacizumab (10 mg/kg, i.v., n=6), or TIC10 and bevacizumab (n=7) at 2 weeks post-implantation.

Table III shows the change in overall survival of mouse cohorts with SF767 intracranial tumors.

TABLE III

| Cohort | n | Median Survival (days) | ΔMedian Survival (days) | P |
|---|---|---|---|---|
| Control | 8 | 28 | — | — |
| TIC10 | 7 | 74 | 46 | 0.038 |
| bev | 6 | 70 | 42 | 0.119 |
| TIC10 + bev | 7 | 96.5 | 68.5 | 0.0308 |

TIC10-Induced TRAIL Upregulation is Foxo3a-Dependent

Figure 50:
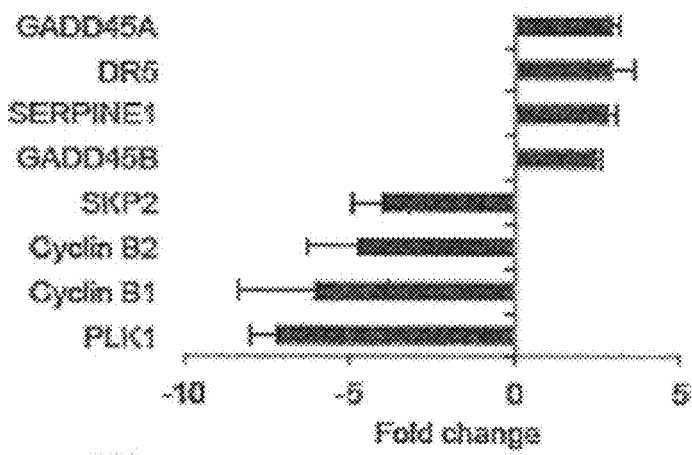
FIG. 50 is a graph showing transcriptional changes associated with FOXO signaling from gene expression profiling of HCT116 p53$^{-/-}$ cells at 48 hr post-TIC10 treatment versus DMSO.

To identify the molecular events underpinning TIC10-induced upregulation of TRAIL, gene expression profiles in TIC10-treated HCT116 p53$^{-/-}$ cells were determined Transcriptional changes in target genes of the FOXO family of transcription factors were observed, which includes Foxo3a that has been previously shown to regulate the TRAIL gene promoter at a binding site contained within the region selected for as described in Modur, V. et al., 2002, J. Biol. Chem. 277:47928-47937. FIG. 50 is a graph showing transcriptional changes associated with FOXO signaling from gene expression profiling of HCT116 p53$^{-/-}$ cells at 48 hr post-TIC10 treatment (10 µM) versus DMSO (n=3). All of these changes were P<0.05 between DMSO and TIC10 treatment groups. Error bars indicate s.d. of replicates. *P<0.05 between the indicated condition and control unless otherwise indicated.

Figure 51:
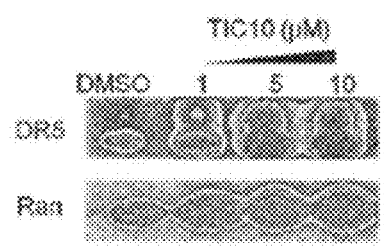
FIG. 51 is an image of Western blot analysis of DR5 in HCT116 cells treated with TIC10 or DMSO.
Figure 52:
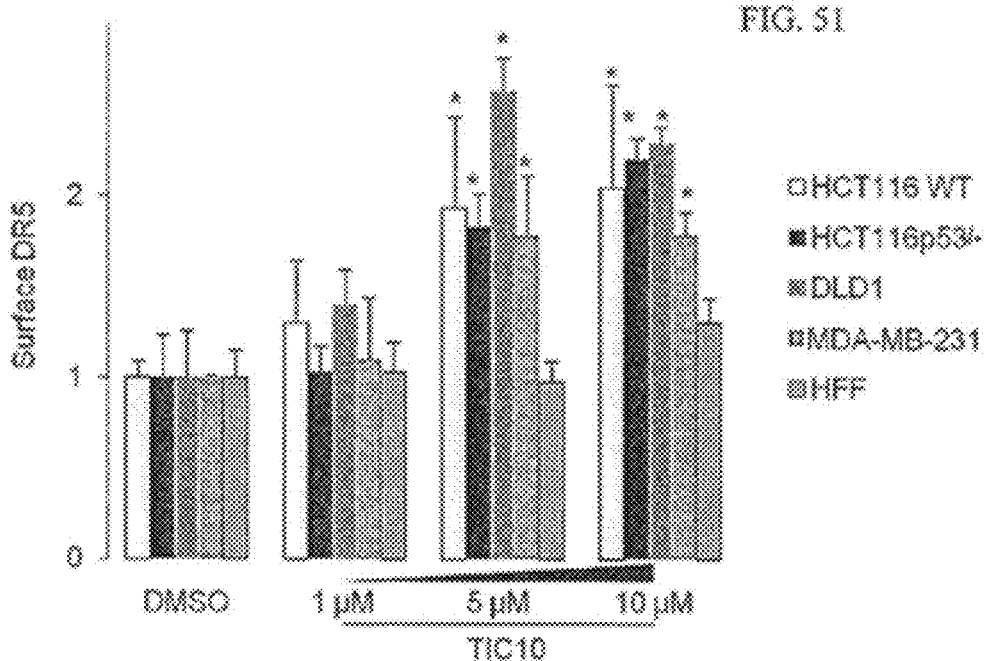
FIG. 52 is a graph showing flow cytometry analysis of surface DR5 levels in cancer and normal cells treated with TIC10.

The FOXO-target gene DR5 was upregulated by TIC10 in several cancer cell lines and to a much lesser extent in normal cells and this was also observed in TIC10-treated tumors. FIG. 51 is an image of Western blot analysis of DR5 in HCT116 cells treated with TIC10 or DMSO at indicated concentrations for 72 hr. Ran is shown as a loading control. FIG. 52 is a graph showing flow cytometry analysis of surface DR5 levels in cancer and normal cells treated with TIC10 (72 hr, n=3). Error bars indicate s.d. of replicates. *P<0.05 between the indicated condition and control unless otherwise indicated.

IHC analysis of DR5 in HCT116 xenograft tumors treated with vehicle (i.p.) or TIC10 (100 mg/kg, i.p.) shows, in agreement with in vitro observations that elevated DR5 expression was evident in TIC10-treated xenograft tumors.

FOXO family members, Foxo3a (but not Foxo1a) underwent a nuclear translocation in response to TIC10 as determined by immunofluorescence and Western blot analysis of Foxo3a in HCT116 cells and immunofluorescence analysis of Foxo3a in H460 and SW480 cells treated with DMSO or TIC10, 10 µM, 48 hr.

Figure 53:
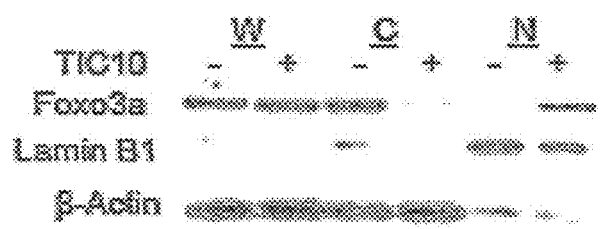
FIG. 53 is an image of Western blot analysis of whole cell lysates (W) and cytoplasmic (C) and nuclear (N) extracts from HCT116 cells treated with DMSO or TIC10.

FIG. 53 is an image of Western blot analysis of whole cell lysates (W) and cytoplasmic (C) and nuclear (N) extracts from HCT116 cells treated with DMSO or TIC10 (48 hr, 10 µM). β-actin and lamin B1 are shown as cytoplasmic and nuclear loading controls, respectively.

Figure 54:
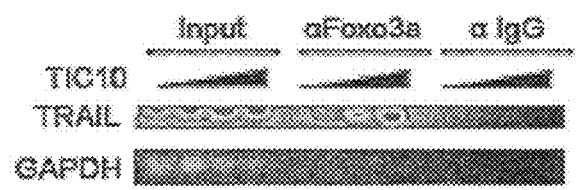
FIG. 54 is an image of results of a chromatin immuno-precipitation assay for TIC10-induced translocation of Foxo3a to the TRAIL promoter at 48 hr post-TIC10 treatment in HCT116 p53$^{-/-}$ cells, 0, 2.5, 5, or 10 μM from left to right.

A TIC10 dose-dependent increase in the amount of Foxo3a localized to the TRAIL promoter was found as shown by chromatin immunoprecipitation assay. FIG. 54 is an image of results of a chromatin immunoprecipitation assay for TIC10-induced translocation of Foxo3a to the TRAIL promoter at 48 hr post-TIC10 treatment in HCT116 p53$^{-/-}$ cells (0, 2.5, 5, or 10 µM from left to right).

Figure 55:
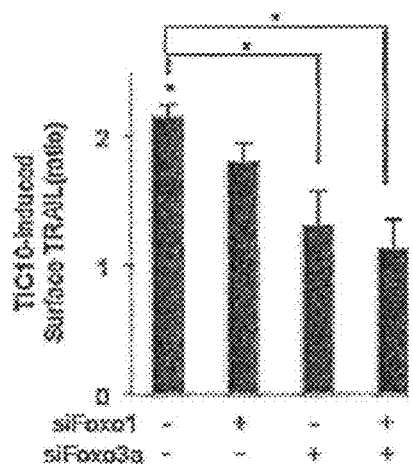
FIG. 55 is a graph showing results of flow cytometry analysis of cell surface TRAIL levels induced by TIC10 with or without transient knockdown of Foxo1 and/or Foxo3a in HCT116 p53$^{-/-}$ cells using siRNA.

Transient knockdown of Foxo3a and Foxo1 revealed that Foxo3a specifically mediated TIC10-induced TRAIL upregulation. FIG. 55 is a graph showing results of flow cytometry analysis of cell surface TRAIL levels induced by TIC10 (10 µM) with or without transient knockdown of Foxo1 and/or Foxo3a in HCT116 p53$^{-/-}$ cells using siRNA (72 hr, n=3). Knockdown is confirmed by Western blot analysis. Error bars indicate s.d. of replicates. *P<0.05 between the indicated condition and control unless otherwise indicated.

Figure 56:
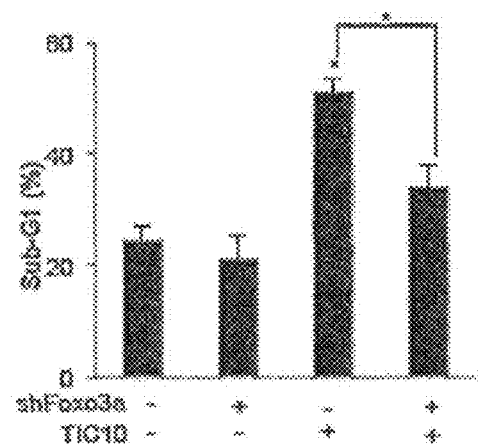
FIG. 56 is a graph showing sub-G1 analysis of TIC10-induced cell death with or without stable knockdown of Foxo3a in HCT116 cells.
Figure 57:
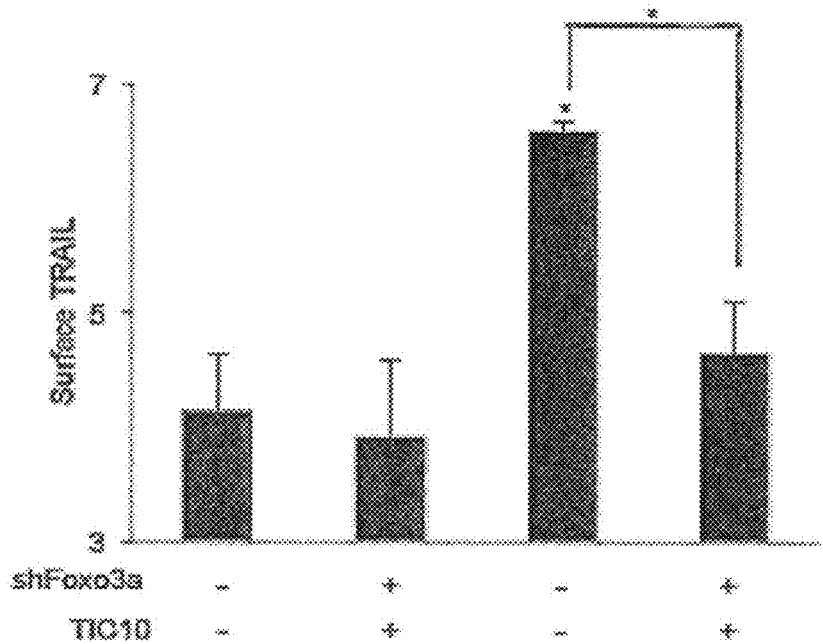
FIG. 57 is a graph showing flow cytometry analysis of TIC10-induced surface TRAIL with or without stable knockdown of Foxo3a in HCT116 cells.

Stable knockdown of Foxo3a significantly inhibited TIC10-induced upregulation of TRAIL production and subsequent tumor cell death. FIG. 56 is a graph showing sub-G1 analysis of TIC10-induced cell death with or without stable knockdown of Foxo3a in HCT116 cells (10 µM, 72 hr, n=3). Error bars indicate s.d. of replicates. *P<0.05 between the indicated condition and control unless otherwise indicated. FIG. 57 is a graph showing flow cytometry analysis of TIC10-induced surface TRAIL with or without stable knockdown of Foxo3a in HCT116 cells (10 µM, 72 hr, n=3). Error bars indicate s.d. of replicates. *P<0.05 between the indicated condition and control unless otherwise indicated. Results of Foxo3a stable knockdown were confirmed by Western blot analysis.

Figure 58:
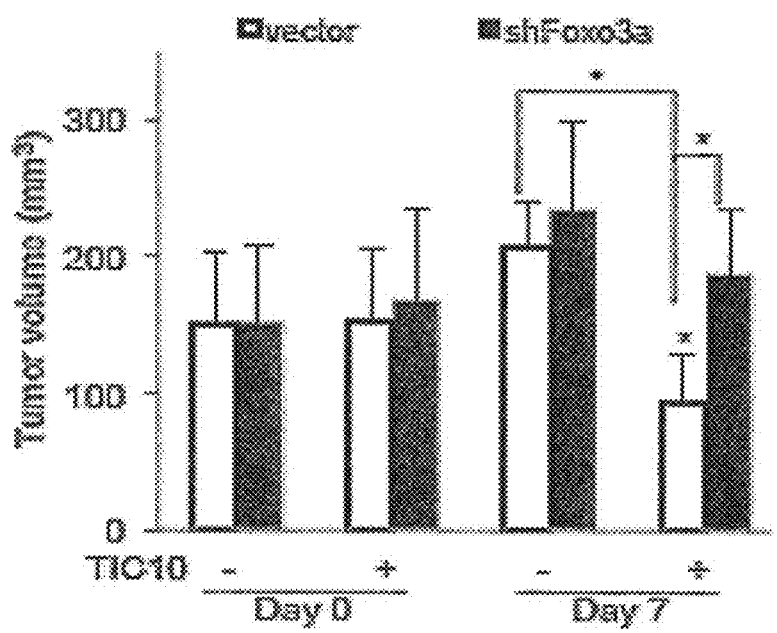
FIG. 58 is a graph showing tumor volume of HCT116 xenograft with or without stable knockdown of Foxo3a following a single oral dose of vehicle or TIC10.

Stable knockdown of Foxo3a in tumor cells also significantly inhibited the anti-tumor activity of TIC10 and TIC10-induced hallmarks of TRAIL-mediated apoptosis in tumors in vivo. FIG. 58 is a graph showing tumor volume of HCT116 xenograft with or without stable knockdown of Foxo3a following a single oral dose of vehicle or TIC10 (25 mg/kg) on day 0 (n=10). Error bars indicate s.d. of replicates. *P<0.05 between the indicated condition and control unless otherwise indicated.

IHC analysis and TUNEL staining of HCT116 tumors with or without stable knockdown of Foxo3a 3 days after a single dose of TIC10 (25 mg/kg, oral) was performed and showed that stable knockdown of Foxo3a in tumor cells also significantly inhibited the anti-tumor activity of TIC10 and TIC10-induced hallmarks of TRAIL-mediated apoptosis in tumors in vivo.

Dual Inactivation of Akt and ERK by TIC10 Cooperatively Induces TRAIL

Figure 59:
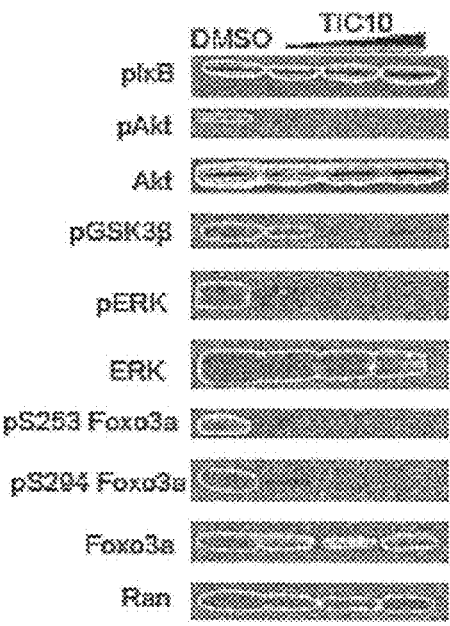
FIG. 59 is an image of Western blot analysis of HCT116 p53$^{-/-}$ cells treated with TIC10, 2.5, 5, 10 μM for 72 hr.

TIC10-induced changes in regulators of Foxo3a such as IKK, Akt, and ERK were determined. FIG. 59 is an image of Western blot analysis of HCT116 p53$^{-/-}$ cells treated with TIC10 (2.5, 5, 10 µM) for 72 hr.

Figure 60:
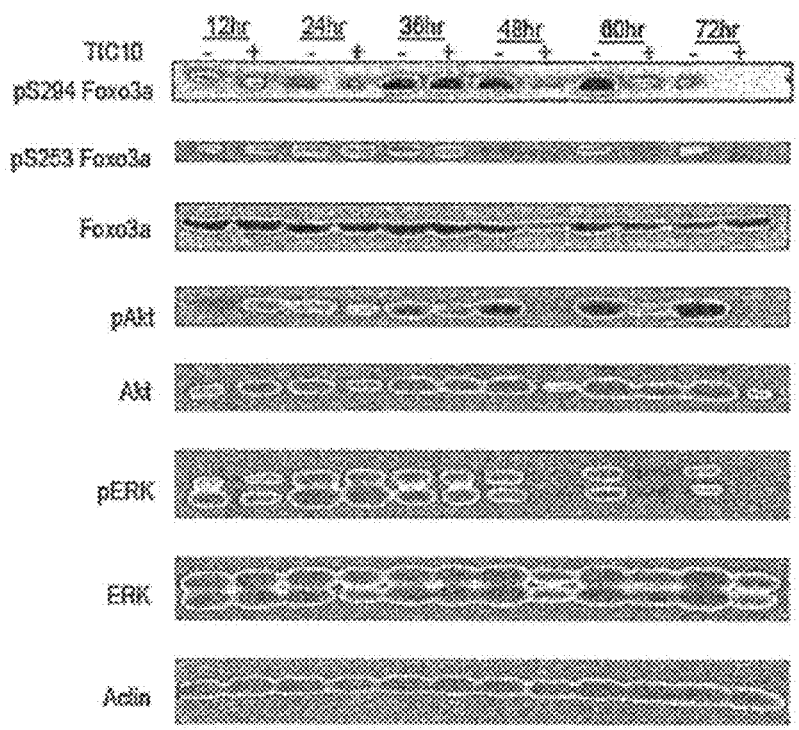
FIG. 60 is an image of Western blot analysis of HCT116 p53$^{-/-}$ cells treated with TIC10.
Figure 61:
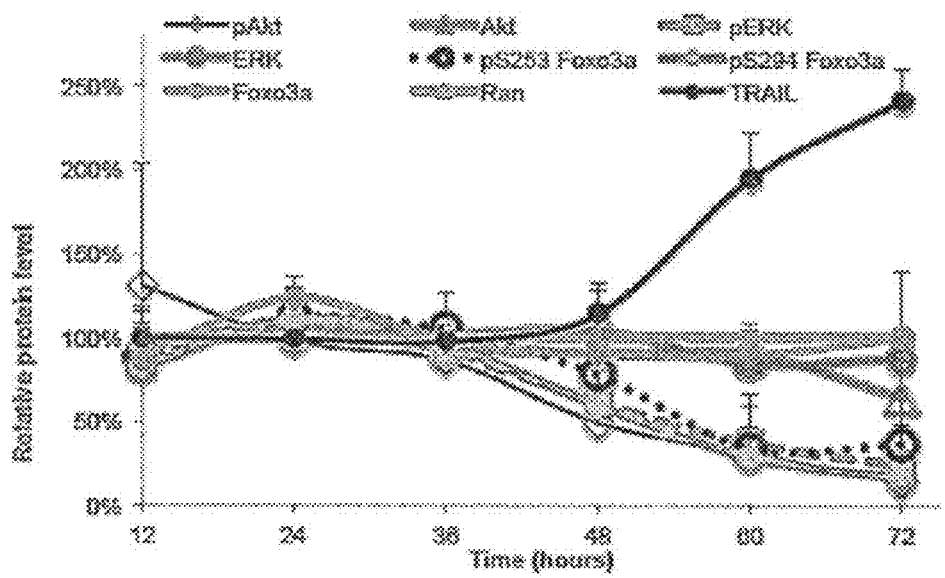
FIG. 61 is a graph showing time course of protein expression levels of TIC10-induced effects determined by densitometry of Western blots from replicate experiments as in FIG. 60.

Both pAkt and pERK levels were found to be abolished with TIC10 treatment in a dose-dependent manner that was accompanied by dephosphorylation of their respective phosphorylation sites on Foxo3a. A time course analysis revealed that TIC10-induced inactivation of Akt and ERK occurred after 48 hours, kinetics that were concerted with the dephosphorylation of Foxo3a and TRAIL upregulation. FIG. 60 is an image of Western blot analysis of HCT116 p53$^{-/-}$ cells treated with TIC10 (10 µM) for indicated time periods. FIG. 61 is a graph showing time course of protein expression levels of TIC10-induced effects determined by densitometry of Western blots from replicate experiments as in FIG. 60 (n=3). Data is express relative to the control sample for each time point and normalized to Ran. TRAIL was quantified by flow cytometry as a parallel experiment (n=3).

Figure 62:
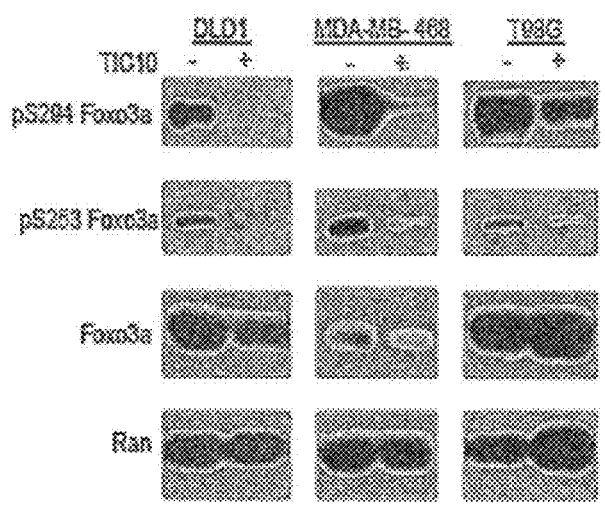
FIG. 62 is an image of Western blot analysis of TIC10-induced effects on Foxo3a in DLD1 human colon cancer cells, MDA-MB-468 human breast cancer cells, and T98G human glioblastoma multiforme cell lines.

These TIC10-induced effects on Foxo3a were evident in several cancer cell lines of different tumor types, which include human cancer cell lines with diverse genetic backgrounds that harbor oncogenic alterations in p53, KRAS, PTEN and others. FIG. 62 is an image of Western blot analysis of TIC10-induced effects on Foxo3a in DLD1 human colon cancer cells, MDA-MB-468 human breast cancer cells, and T98G human glioblastoma multiforme cell lines (10 µM, 72 hr).

Figure 63:
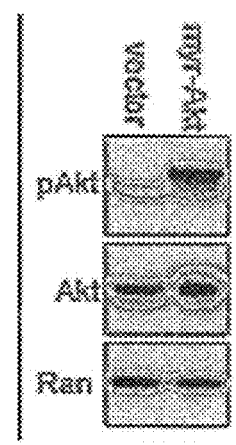
FIG. 63 is an image of Western blot analysis showing overexpression of myr-Akt.
Figure 64:
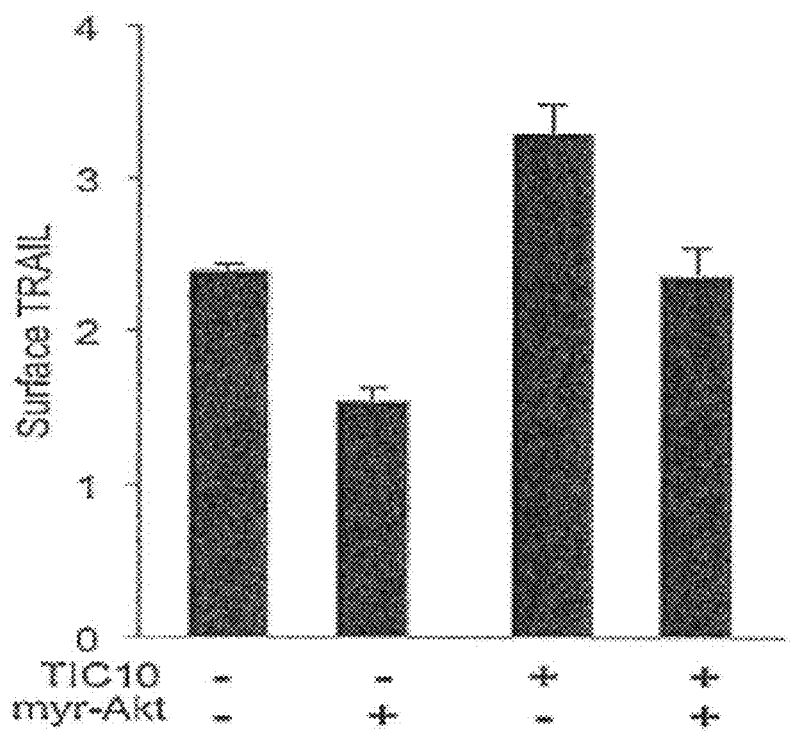
FIG. 64 is a graph showing flow cytometry analysis of surface TRAIL in HCT116 cells overexpressing an empty vector or myristilated Akt (myr-Akt) with TIC10 treatment.
Figure 65:
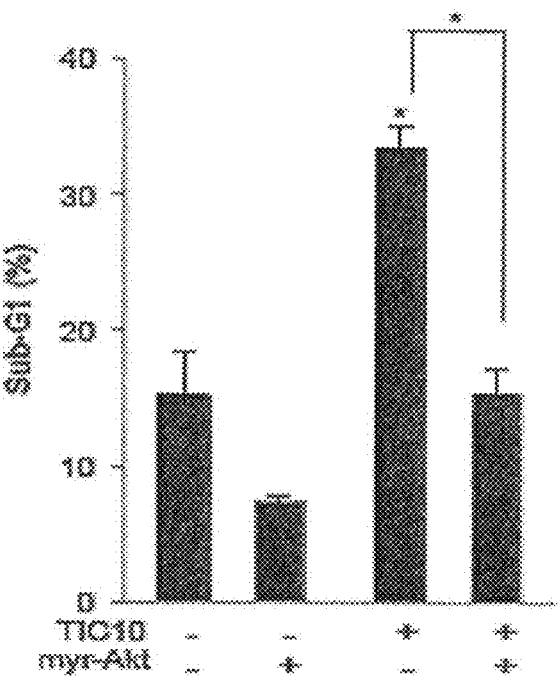
FIG. 65 is a graph showing sub-G1 content of HCT116 cells overexpressing an empty vector or myr-Akt with TIC10 treatment.

Akt is found to be a determinant of cytotoxic sensitivity to TIC10 and its TRAIL upregulation, and overactivating Akt can suppress even basal levels of TRAIL as shown by immunofluorescence analysis of Foxo3a in HCT116 cells overexpressing an empty vector or myristilated Akt (myr-Akt) with TIC10 treatment (10 µM, 48 hr). Confirmation of overexpression of myr-Akt by Western blot analysis is shown in FIG. 63. FIG. 64 is a graph showing flow cytometry analysis of surface TRAIL in HCT116 cells overexpressing an empty vector or myristilated Akt (myr-Akt) with TIC10 treatment (10 µM, 48 hr). FIG. 65 is a graph showing sub-G1 content of HCT116 cells overexpressing an empty vector or myr-Akt with TIC10 treatment (10 µM, 72 hr, n=3).

Figure 66:
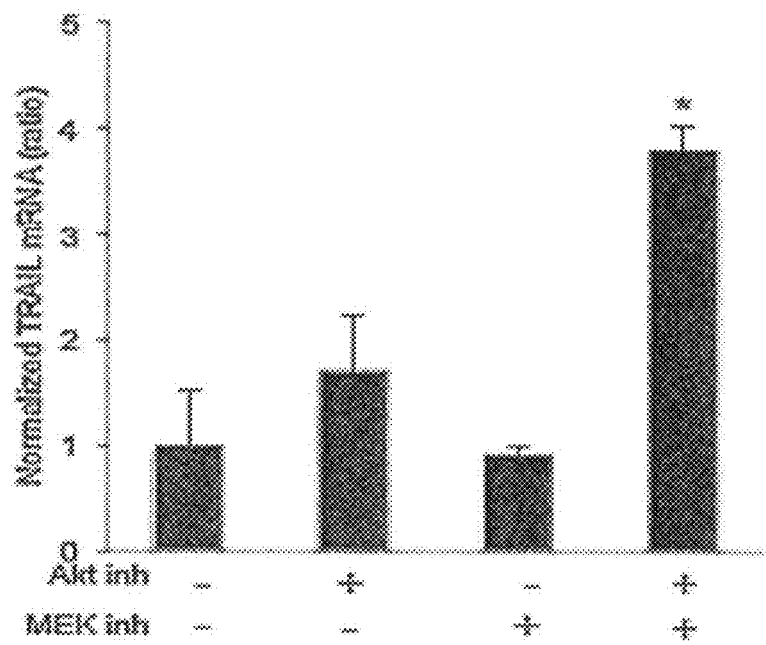
FIG. 66 is a graph showing RT-qPCR analysis of TRAIL mRNA in HCT116 p53$^{-/-}$ cells following incubation with A6730 (Akt inh), U0126 monoethanolate (MEK inh), or both.

Dual inhibition of the Akt and the MAPK pathways will cooperatively lead to the nuclear translocation of Foxo3a and ensuing TRAIL upregulation. A6730 and U0126 monoethanolate are commercially available and previously described inhibitors of Akt1/2, Desplat, V. et al., 2008, J. Enz. Inhib Med. Chem., 23: 648-658, and MEK, Favata, M. F., et al., 1998, J. Biol. Chem., 273:18623-18632, respectively used in this example to determine if dual inhibition of the Akt and the MAPK pathways will cooperatively lead to the nuclear translocation of Foxo3a and ensuing TRAIL upregulation. The combination of MEK and Akt inhibitors was found to cooperatively induce Foxo3a-dependent TRAIL upregulation and synergistically TRAIL-mediated cell death. FIG. 66 is a graph showing RT-qPCR analysis of TRAIL mRNA in HCT116 p53$^{-/-}$ cells following incubation with 10 μM A6730 (Akt inh), U0126 monoethanolate (MEK inh), or both (48 hr, n=3). For Akt+MEK inh, $P<0.05$ compared to all other conditions. *$P<0.05$ between the indicated condition and control unless otherwise indicated.

Figure 67:
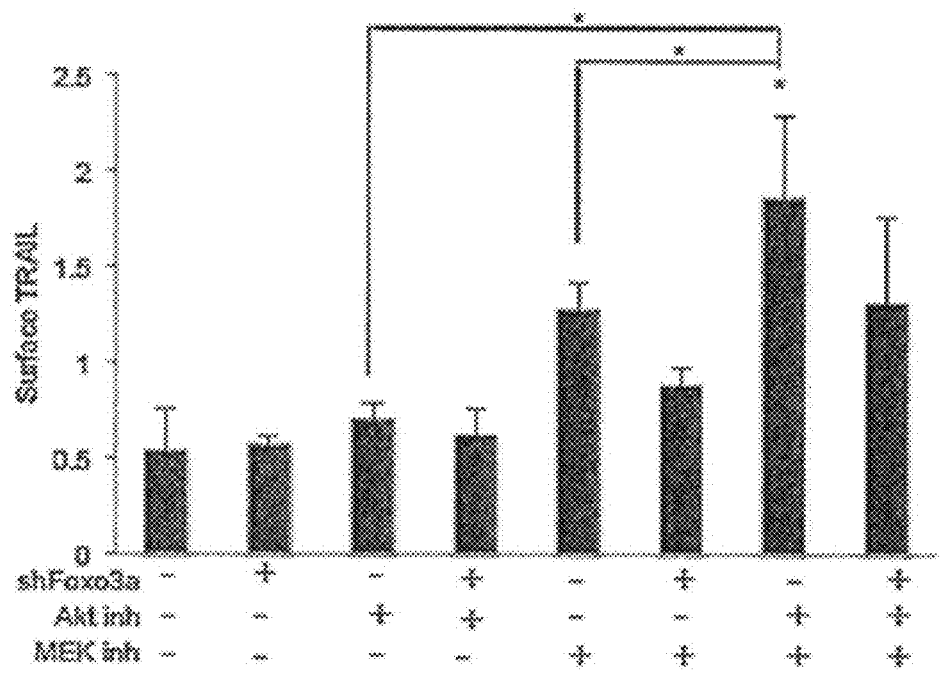

FIG. 67 is a graph showing surface TRAIL induction as in FIG. 66 with or without stable knockdown of Foxo3a (n=3). *$P<0.05$ between the indicated condition and control unless otherwise indicated.

Figure 68:
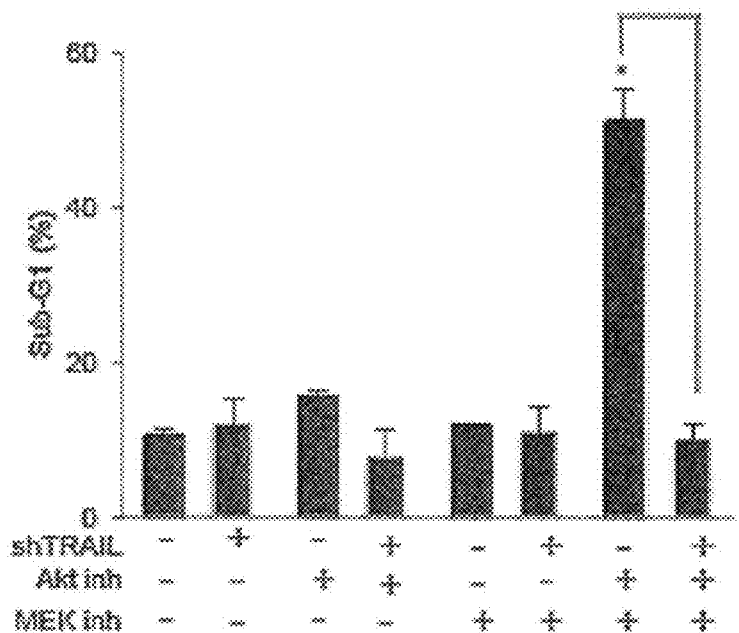
FIG. 68 is a graph showing sub-G1 analysis of MDA-MB-231 with or without TRAIL knockdown by shRNA following incubation with Akt inh, MEK inh, or both.
Figure 69:
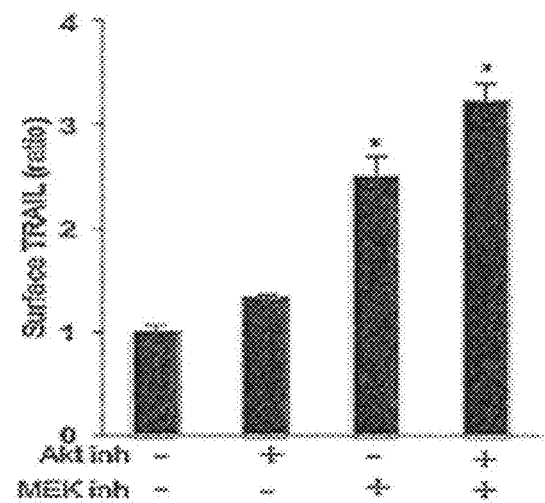
FIG. 69 is a graph showing surface TRAIL analysis of HCT116 p53$^{-/-}$ cells following incubation with A6730 (Akt inh), U0126 monoethanolate (MEK inh), or both.
Figure 70:
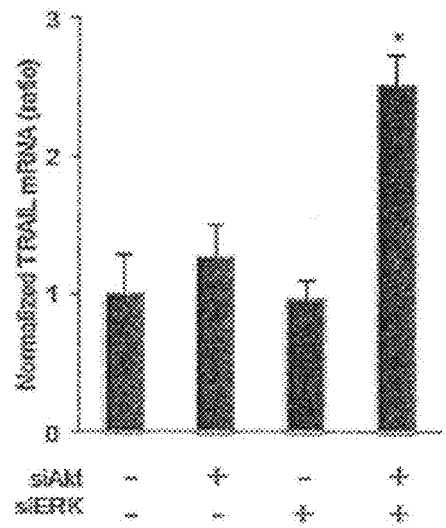
FIG. 70 is a graph showing RT-qPCR analysis of TRAIL mRNA levels following transient knockdown of Akt and/or ERK in HCT116 p53$^{-/-}$ cells.

FIG. 68 is a graph showing sub-G1 analysis of MDA-MB-231 with or without TRAIL knockdown by shRNA following incubation with 10 μM Akt inh, MEK inh, or both for 48 hr (n=3). *$P<0.05$ between the indicated condition and control unless otherwise indicated. FIG. 69 is a graph showing surface TRAIL analysis of HCT116 p53$^{-/-}$ cells following incubation with 10 μM A6730 (Akt inh), U0126 monoethanolate (MEK inh), or both (48 hr, n=3).

siRNA experiments in this example show that ERK and Akt can be inhibited to cooperatively upregulate TRAIL. FIG. 70 is a graph showing RT-qPCR analysis of TRAIL mRNA levels following transient knockdown of Akt and/or ERK in HCT116 p53$^{-/-}$ cells at 48 hr post-knockdown (n=3). For siERK and siAkt combination, $P<0.05$ compared to all other conditions.

Figure 71:
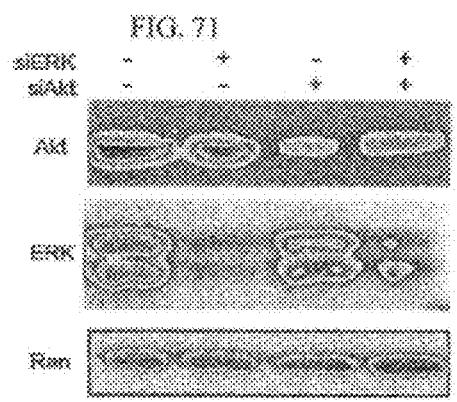
FIG. 71 is an image showing confirmation of Akt and ERK knockdown by Western blot analysis.
Figure 72:
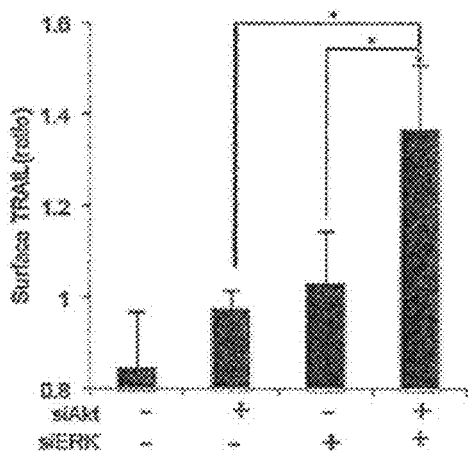
FIG. 72 is a graph showing surface TRAIL analysis following transient knockdown of Akt and/or ERK in HCT116 cells.

FIG. 71 is an image showing confirmation of Akt and ERK knockdown by Western blot analysis. Error bars indicate s.d. of replicates. FIG. 72 is a graph showing surface TRAIL analysis following transient knockdown of Akt and/or ERK in HCT116 cells at 48 hr post-knockdown (n=3).

TIC10 causes a dual inactivation of Akt and ERK, which cooperatively leads to the nuclear translocation of their mutual substrate Foxo3a that transcriptionally induces the TRAIL gene as a unique target gene to potentiate cell death and potent anti-tumor effects in vivo.

Any patents or publications mentioned in this specification are incorporated herein by reference to the same extent as if each individual publication is specifically and individually indicated to be incorporated by reference.

The compositions and methods described herein are presently representative of preferred aspects, exemplary, and not intended as limitations on the scope of the invention. Changes therein and other uses will occur to those skilled in the art. Such changes and other uses can be made without departing from the scope of the invention as set forth in the claims.

The invention claimed is:

1. A method of treating a subject having cancer, comprising:
   administering to the subject a pharmaceutical composition comprising a pharmaceutically effective amount of:

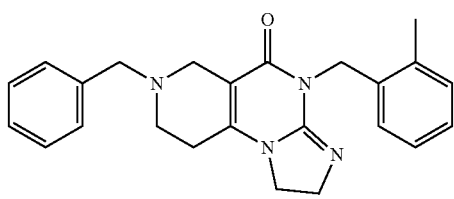

(I)

or a pharmaceutically acceptable salt, hydrate, and/or solvate thereof, wherein the cancer is adenocarcinoma.

2. The method of claim 1, wherein the subject has a pre-neoplastic hyperproliferation, a cancer in-situ, a neoplasm or a metastasis.

3. The method of claim 1, wherein the cancer is a metastatic cancer.

4. The method of claim 1, wherein the cancer is a grade IV cancer.

5. The method of claim 1, wherein the cancer is a late stage cancer.

6. The method of claim 1, wherein the cancer harbors an oncogenic alteration.

7. The method of claim 6, wherein the oncogenic alteration is inactivation of a tumor suppressor.

8. The method of claim 7, wherein p53 is inactivated.

9. The method of claim 7, wherein PTEN is inactivated.

10. The method of claim 6, wherein the oncogenic alteration is activation of an oncogene.

11. The method of claim 10, wherein EGFR, Her2, and/or KRAS is mutated.

12. The method of claim 1, further comprising administering a second therapeutic to the subject, wherein the second therapeutic comprises an anti-cancer agent.

13. The method of claim 12, wherein the anti-cancer agent is a mitotic inhibitor.

14. The method of claim 12, wherein the anti-cancer agent is selected from the group consisting of paclitaxel, docetaxel, and a combination thereof.

15. The method of claim 1, further comprising administering a second therapeutic to the subject, wherein the second therapeutic comprises an anti-angiogenic agent.

16. The method of claim 15, wherein the anti-angiogenic agent is bevacizumab.

17. The method of claim 1, wherein the pharmaceutical composition is administered orally.

18. The method of claim 1, wherein the pharmaceutical composition is administered via a route of administration selected from the group consisting of rectal, nasal, pulmonary, epidural, ocular, otic, intraarterial, intracardiac, intracerebroventricular, intradermal, intravenous, intramuscular, intraperitoneal, intraosseous, intrathecal, intravesical, subcutaneous, topical, transdermal, transmucosal, sublingual, buccal, vaginal, and inhalational routes of administration.

19. The method of claim 1, wherein the pharmaceutical composition further comprises a pharmaceutically acceptable carrier.

20. The method of claim 1, wherein the pharmaceutical composition is a solid dosage form.

21. The method of claim 1, wherein the pharmaceutical composition is a liquid dosage form.

22. The method of claim 21, wherein the liquid dosage form is an injectable liquid.

* * * * *